US012396839B2

(12) United States Patent
Connor et al.

(10) Patent No.: US 12,396,839 B2
(45) Date of Patent: Aug. 26, 2025

(54) METHOD AND APPARATUS FOR CREATING A SEAM-LIKE ANATOMICAL LOW CREEP ATTACHMENT OF SOFT TISSUE TO BONE

(71) Applicant: Integrity Orthopaedics, Inc., Orono, MN (US)

(72) Inventors: Patrick M. Connor, Charlotte, NC (US); Howard W. Harris, Southlake, TX (US); Marc Labbé, Spring, TX (US); Thomas A. Westling, Orono, MN (US); Zak Zenz-Olson, Ham Lake, MN (US); Nathaniel Van Tran, Lakeville, MN (US); David M. Crompton, St. Paul, MN (US)

(73) Assignee: Integrity Orthopaedics, Inc., Maple Plain, MN (US)

( * ) Notice: Subject to any disclaimer, the term of this patent is extended or adjusted under 35 U.S.C. 154(b) by 855 days.

(21) Appl. No.: 17/681,430

(22) Filed: Feb. 25, 2022

(65) Prior Publication Data

US 2022/0323200 A1    Oct. 13, 2022

Related U.S. Application Data

(63) Continuation-in-part of application No. 17/551,779, filed on Dec. 15, 2021, now Pat. No. 11,382,612.

(60) Provisional application No. 63/281,411, filed on Nov. 19, 2021, provisional application No. 63/172,614, filed on Apr. 8, 2021.

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0414* (2013.01)

(58) Field of Classification Search
CPC ........ A61B 17/0401; A61B 2017/0404; A61B 2017/0406; A61B 2017/0408; A61B 2017/0414; A61B 2017/0417; A61B 2017/0419; A61B 2017/0445; A61B 2017/0446; A61B 2017/0458; A61F 2/0811
See application file for complete search history.

(56) References Cited

U.S. PATENT DOCUMENTS

| 4,899,743 A | 2/1990 | Nicholson et al. |
| 4,968,315 A | 11/1990 | Gatturna |
| 5,041,129 A | 8/1991 | Hayhurst et al. |

(Continued)

*Primary Examiner* — Dianne Dornbusch
(74) *Attorney, Agent, or Firm* — Seager, Tufte & Wickhem LLP

(57) ABSTRACT

Methods and apparatus for creating a seam like array of suture stitches joined in series by sequential anchors in bone. The anchors are transtendon implants positioned through the tendon in the original tendon footprint and each array includes four or more anchors. The seam like array extends across at least a portion of the tendon. The stitches can extend generally perpendicular to the direction of the tendon orientation. In rotator cuff repair, the anchors are positioned in the original footprints of the infraspinatus and/or supraspinatus tendons and the seam like array extends in an anterior to posterior direction across the particular tendons torn and repaired. The entire array of anchors can be positioned in the medial half of the original footprints.

20 Claims, 21 Drawing Sheets

(56) References Cited

U.S. PATENT DOCUMENTS

| | | |
|---|---|---|
| 5,192,303 A | 3/1993 | Gatturna et al. |
| 5,203,787 A | 4/1993 | Noblitt et al. |
| 5,207,679 A | 5/1993 | Li |
| 5,269,809 A | 12/1993 | Hayhurst et al. |
| 5,403,348 A | 4/1995 | Bonutti |
| 5,405,359 A | 4/1995 | Pierce |
| 5,464,426 A * | 11/1995 | Bonutti .............. A61B 17/0401 606/232 |
| 5,468,197 A | 11/1995 | Loeffler |
| 5,584,835 A | 12/1996 | Greenfield |
| 5,626,614 A | 5/1997 | Hart |
| 5,669,935 A | 9/1997 | Rosenman et al. |
| 5,683,418 A | 11/1997 | Luscombe et al. |
| 5,725,557 A | 3/1998 | Gatturna et al. |
| 5,728,100 A | 3/1998 | Skiba |
| 5,741,300 A | 4/1998 | Li |
| 5,810,848 A | 9/1998 | Hayhurst |
| 5,891,168 A * | 4/1999 | Thal .................. A61B 17/0401 606/232 |
| 5,921,986 A | 7/1999 | Bonutti |
| 5,948,002 A | 9/1999 | Bonutti |
| 5,961,538 A | 10/1999 | Pedlick et al. |
| 6,056,773 A | 5/2000 | Bonutti |
| 6,066,160 A | 5/2000 | Colvin et al. |
| 6,117,161 A | 9/2000 | Li et al. |
| 6,149,669 A * | 11/2000 | Li ...................... A61B 17/0401 606/68 |
| 6,270,518 B1 | 8/2001 | Pedlick et al. |
| 6,293,961 B2 | 9/2001 | Schwartz et al. |
| 6,451,030 B2 | 9/2002 | Li et al. |
| 6,500,195 B2 | 12/2002 | Bonutti |
| 6,520,980 B1 | 2/2003 | Foerster |
| 6,527,795 B1 | 3/2003 | Lizardi |
| 6,547,800 B2 | 4/2003 | Foerster et al. |
| 6,592,609 B1 | 7/2003 | Bonutti |
| 6,645,227 B2 | 11/2003 | Fallin et al. |
| 6,660,023 B2 | 12/2003 | McDevitt et al. |
| 6,726,707 B2 | 4/2004 | Pedlick et al. |
| 6,773,436 B2 | 8/2004 | Donnelly et al. |
| 6,843,799 B2 | 1/2005 | Bartlett |
| 6,972,027 B2 | 12/2005 | Fallin et al. |
| 6,986,781 B2 | 1/2006 | Smith |
| 7,041,120 B2 | 5/2006 | Li et al. |
| 7,081,126 B2 | 7/2006 | McDevitt et al. |
| 7,232,455 B2 | 6/2007 | Pedlick et al. |
| 7,320,701 B2 | 1/2008 | Haut et al. |
| 7,556,640 B2 | 7/2009 | Foerster |
| 7,566,339 B2 | 7/2009 | Fallin et al. |
| 7,641,672 B2 | 1/2010 | Fallin et al. |
| 7,645,293 B2 | 1/2010 | Martinek et al. |
| 7,674,275 B2 | 3/2010 | Martin et al. |
| 7,682,374 B2 | 3/2010 | Foerster et al. |
| 7,722,644 B2 | 5/2010 | Fallin et al. |
| 7,806,909 B2 | 10/2010 | Fallin et al. |
| 7,875,064 B2 | 1/2011 | Donnelly et al. |
| 7,909,851 B2 | 3/2011 | Stone et al. |
| 7,963,972 B2 | 6/2011 | Foerster et al. |
| 8,052,719 B2 | 11/2011 | Paulos |
| 8,118,835 B2 | 2/2012 | Weisel et al. |
| 8,298,262 B2 | 10/2012 | Stone et al. |
| 8,348,975 B2 | 1/2013 | Dreyfuss |
| 8,366,744 B2 | 2/2013 | Bojarski et al. |
| 8,419,794 B2 | 4/2013 | ElAttrache et al. |
| 8,425,536 B2 | 4/2013 | Foerster et al. |
| 8,449,584 B2 | 5/2013 | Donnelly et al. |
| 8,454,655 B2 | 6/2013 | Yeung et al. |
| 8,512,375 B2 | 8/2013 | Torrie et al. |
| 8,771,314 B2 | 7/2014 | Crombie et al. |
| 8,777,992 B2 | 7/2014 | Yeung et al. |
| 8,828,052 B2 | 9/2014 | Caborn et al. |
| 8,828,054 B2 * | 9/2014 | Caborn .............. A61B 17/0483 606/232 |
| 8,845,699 B2 | 9/2014 | Bonutti |
| 8,932,331 B2 | 1/2015 | Kaiser et al. |
| 8,951,287 B1 | 2/2015 | Green et al. |
| 8,986,346 B2 | 3/2015 | Dreyfuss |
| 9,072,509 B2 | 7/2015 | Stoll, Jr. et al. |
| 9,173,651 B2 | 11/2015 | Stone et al. |
| 9,192,369 B2 | 11/2015 | Bittenson |
| 9,216,036 B2 | 12/2015 | Johnstone |
| 9,220,493 B2 | 12/2015 | Hart et al. |
| 9,265,495 B2 | 2/2016 | Petersen et al. |
| 9,271,714 B2 | 3/2016 | Martin |
| 9,301,756 B2 | 4/2016 | Wardle |
| 9,307,979 B1 | 4/2016 | Bennett et al. |
| 9,314,238 B2 | 4/2016 | Martin |
| 9,345,467 B2 | 5/2016 | Lunn et al. |
| 9,451,945 B2 | 9/2016 | Hawkins |
| 9,463,008 B2 | 10/2016 | Thal |
| 9,504,462 B2 | 11/2016 | Dooney, Jr. et al. |
| 9,526,489 B2 | 12/2016 | Burkhart |
| 9,532,777 B2 | 1/2017 | Kaiser et al. |
| 9,539,000 B2 | 1/2017 | Hendricksen et al. |
| 9,545,251 B2 | 1/2017 | Bojarski et al. |
| 9,597,070 B2 | 3/2017 | Bittenson |
| 9,655,611 B2 | 5/2017 | Green et al. |
| 9,693,765 B2 | 7/2017 | Sullivan et al. |
| 9,713,463 B2 | 7/2017 | Oren et al. |
| 9,763,719 B2 | 9/2017 | Snyder et al. |
| 9,814,565 B2 | 11/2017 | Foerster et al. |
| 9,872,678 B2 | 1/2018 | Spenciner et al. |
| 9,931,150 B2 | 4/2018 | Philippon et al. |
| 10,130,354 B2 | 11/2018 | Dooney, Jr. |
| 10,172,607 B2 | 1/2019 | Burkhart |
| 10,178,989 B2 | 1/2019 | Bennett et al. |
| 10,285,684 B2 | 5/2019 | Spenciner et al. |
| 10,368,856 B2 | 8/2019 | Stone et al. |
| 10,376,260 B2 | 8/2019 | Bojarski et al. |
| 10,398,428 B2 | 9/2019 | Denham et al. |
| 10,478,172 B1 | 11/2019 | Williams et al. |
| 10,543,075 B2 | 1/2020 | Gregoire et al. |
| 10,575,842 B2 | 3/2020 | Lund |
| 10,588,614 B2 | 3/2020 | Gittings et al. |
| 10,603,029 B2 | 3/2020 | Kaiser et al. |
| 10,667,803 B2 | 6/2020 | Lizardi |
| 10,675,015 B2 | 6/2020 | Guo et al. |
| 10,729,421 B2 | 8/2020 | Stone et al. |
| 10,772,622 B2 | 9/2020 | Santangelo et al. |
| 10,786,235 B2 | 9/2020 | Sorensen et al. |
| 10,863,979 B2 | 12/2020 | Sorensen et al. |
| 10,952,719 B2 | 3/2021 | Lombardo et al. |
| 10,966,704 B2 * | 4/2021 | Lozier ................ A61B 17/0483 |
| 10,987,099 B2 | 4/2021 | Stone et al. |
| 2003/0088272 A1 * | 5/2003 | Smith ................ A61B 17/0401 606/232 |
| 2006/0178702 A1 | 8/2006 | Pierce et al. |
| 2009/0312782 A1 | 12/2009 | Park |
| 2013/0190815 A1 | 7/2013 | Mansmann |
| 2015/0250470 A1 * | 9/2015 | Vargas ............... A61B 17/0401 606/232 |
| 2020/0253715 A1 | 8/2020 | Trenhaile |
| 2020/0315775 A1 | 10/2020 | Pilgeram et al. |

\* cited by examiner

METHOD AND APPARATUS FOR CREATING A SEAM-LIKE ANATOMICAL LOW CREEP ATTACHMENT OF SOFT TISSUE TO BONE

CROSS REFERENCE TO RELATED APPLICATIONS

The present application claims the benefit of and priority to U.S. Prov. Pat. App. No. 63/172,614, filed Apr. 8, 2021, titled METHOD FOR CREATING A TENSIONABLE AND LOCKABLE SUTURE ANCHOR ARRAY FOR ANATOMICAL ATTACHMENT OF TISSUE TO BONE, U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE and is a continuation-in-part of U.S. patent application Ser. No. 17/551,779, filed Dec. 15, 2021, now U.S. Pat. No. 11,382,612, titled Method FOR CREATING A TENSIONABLE AND LOCKABLE SUTURE ANCHOR ARRAY FOR ANATOMICAL ATTACHMENT OF TISSUE TO BONE, the disclosures of which are incorporated herein by reference.

BACKGROUND

Throughout the human body there are many attachments of soft tissue, such as tendons and ligaments, to bone as integral elements of motion in functioning joints such as the shoulder. The shoulder joint includes the humeral head of the upper arm bone in contact with the indentation of the glenoid working in conjunction with the rotator cuff, which is a combination of muscles and tendons forming a capsule that both stabilizes the joint and causes desired motion. Injury to the connection between tendons of the rotator cuff muscles to the humeral head, usually a tear in a tendon, is common. These tears do not self-heal. It is estimated that in the U.S. over 4 million people annually are referred to a surgeon due to shoulder pain and over 500,000 of these referrals result in shoulder surgery to repair the rotator cuff.

Significant effort has been expended over the past 30 years to develop bone and tissue anchor devices and methods to respond to the need for effective rotator cuff repair. Early methods and devices utilized an open surgical technique that required a large incision of 4 to 6 cm and cutting the deltoid muscle, then re-attaching after the rotator cuff repair. This method is still used today for massive tears by some surgeons due to high success rate, however, the procedure is associated with deltoid dysfunction, significant pain during recovery and extensive rehabilitation time. Due to the invasiveness of the open surgery and resulting rehabilitation time, a "mini-open" procedure and associated devices were developed in the early 1990's, wherein the surgeon uses partial arthroscopic techniques followed by an incision and split of the deltoid muscle fibers to access the rotator cuff tendon for repair. By the late 1990's, devices and instruments were further developed to complete the repair of rotator cuff tendon attachment to bone using all-arthroscopic techniques, with further resultant reduction in trauma and recovery time.

Arthroscopic repair of the rotator cuff tendon attachments to the humeral head are the most common technique used today. However, it is recognized that these all-arthroscopic techniques are quite difficult to perform and achieve varying results. The skill of the surgeon with the technology available is a known factor related to the procedure's success. Even with the last 20 years of all-arthroscopic technologic advancement and experience, deficiencies persist as evidenced by studies indicating an overall average rotator cuff repair failure rate of 20% to 40%, with a highly variable range of 4% to 90% in individual studies. The study results indicate failure rates are much higher for large or massive tendon tears and there are vast variations in failure rates between surgeons, as well as with respect to various patient factors, equipment used, and type of repair completed.

There is significant controversy among professionals as to the reasons for the high incidence of arthroscopic rotator cuff repair failure (i.e. "re-tear of the rotator cuff"). However, studies clearly show there is a need to reduce the failure rate of arthroscopic rotator cuff repair to avoid its effects of patients' lack of mobility, functional deficits, increased pain and/or requiring subsequent and more invasive surgery with the attendant pain and rehabilitation. In particular, there is great concern for patients who have some degree of native tendon or repair tendon failure yet choose to "live with it" rather than going through a first or additional surgery and rehabilitation, thus affecting quality of life and promoting continued joint degradation from lack of use.

The basic device or devices used for repair of a tendon torn from a bone is one or more suture anchors in which a mechanical structure provides an anchor to the bone and a suture or sutures extend therefrom for attachment to the soft tissue or tendon. Many types of anchor technologies have been proposed and used in procedures. A review of the prior art patent literature indicates over a thousand designs for suture anchors, bone anchors, tendon repair systems, delivery devices and methods espousing improved features over the past 25 years, yet repair failure rate is still unacceptable indicating the need for further improvement in the area of arthroscopic reattachment of tendons to bone and in particular in rotator cuff repair.

Applicants have identified at least two major issues with prior suture anchors and methods of repairing rotator cuff tears. First, prior repairs are not anatomical, meaning the tendon is pulled down onto the bone in a different position and way than the original tendon attachment. With prior methods, the re-attached tendon can be offset from the original footprint of prior attachment and can be laid down in a way that include folds and creases not previously present at the interface between tendon and bone. These issues inhibit healing attachment. The non-anatomical repair is due to the fact that existing anchors with sutures extending therefrom are implanted into bone through the hole formed by the torn tendon. After the anchor is implanted, the surgeon uses suture passers to get ends of the suture through the tendon for securing the tendon. However, this requires that the surgeon approximate where to pass the suture through the tendon so that it pulls the tendon to the correct spot on the footprint. This must be done with each suture and results in tendons being pulled down in ways not matching the original anatomical structure and includes creases in the tendon and gaps where the tendon is not compressed to the bone.

Second, the passed sutures must extend from just a few anchor points within the original tendon footprint due to the size of prior anchors and the need to implant through the hole in the tendon because prior anchors are not implanted through a tendon due to difficulty and potential tendon damage. With prior systems the number of points of attachment in the original footprint are few and there is significant distance across each bridge from anchor to anchor. This results in weak compression at limited locations so that the tendon is not firmly or robustly held against the bone and during use the tendon moves relative to the bone (cyclic creep) which interrupts or prevents healing.

Overview

The present inventors have recognized, among other things, that a problem to be solved is the need for new and/or alternative devices and methods for arthroscopically affixing a tendon or other soft tissue to bone such as in rotator cuff repair with low failure rate, preferably under 10% on average, with little variation between surgeons, patient characteristics, and the system/method used for repair. The disclosed devices, systems, and methods, along with a statement of the problem being solved by each element are included in summary form followed by a description of specific claimed structure or methods in the present disclosure. Importantly, the invention is directed to a system and method wherein the implanted array of anchors, with a continuous set of anchor-to-anchor serial single suture stitches therebetween, creates a seam-like attachment of tendon to bone akin to a seam created by a sewing machine in fabric.

The seam-like attachment is anatomic in that the tendon area that was torn from the humeral head is laid down in continuous contact with the original footprint on the humeral head without creases and folds. Anchors are then implanted through the tendon (transtendon) as properly positioned to maintain flat continuous contact with the bone. Further, as the anchors do not require installation through the hole formed by the torn tendon, there is not the same limit on the number of anchors that can be utilized to get anatomical attachment. Also, there is no suture passing (wherein the tendon is pulled down onto bone based on an approximation of proper position) because the suture is inserted through the tendon into the bone beneath it.

The system also uses a single suture strand (sometimes referred to as the working suture) in each array serially connecting a significantly increased number of anchors rather than multiple strands of suture extending from a few anchors to be attached at angles to distant anchors outside the footprint. This results in stronger, more vertical compression at increased numbers of locations so that the tendon is firmly and robustly held against the bone. Post-surgery, the tendon has little or no cyclic creep (movement relative to the bone) to maintain healing contact at the bone and tendon interface.

The combination of discontinuous tendon contact with the humeral head and micromotion of the tendon on the humeral head during use are believed to be significant sources of failure to heal properly in prior repairs with subsequent re-tear or failure. To address these issues the currently disclosed system and method utilizes six features and/or implantation techniques to assure continuous tendon/bone contact and minimal micromotion. These include:
1. The implants are designed for and implanted transtendon (through the positioned tendon). Each of the anchors is implanted within the original tendon footprint where bone quality is generally better for an individual patient. In rotator cuff repair, the anchors are preferably implanted in the original footprints of the supraspinatus and infraspinatus tendons with preferred location in the medial half of the original footprint.
2. The anchors are implanted in a row across at least a portion of the tendon with serial stitches extending continuously from one anchor to the next to create the seam like array of stitches. In the rotator cuff, the seam generally extends in the anterior to posterior direction across the tendon which can be generally perpendicular to the tendon fiber orientation or direction of tendon function.
3. The anchor insertion size is small so that they can be implanted in a high-density array with significantly greater numbers within the original footprint in close proximity to each other. Preferred distance between anchors is less than 7 millimeters (mm) from edge of bone hole to edge of bone hole or less than 10 mm from center of bone hole to center of adjacent bone hole. With this spacing the anchors are sized to fit within bone holes less than or equal to about 3 mm in diameter. The high density and close proximity of anchors in the original footprint creates short serial stitches between sequential anchors that apply force more vertically to hold the tendon firmly against bone within the original tendon footprint.
4. Each anchor-to-anchor stitch is tensioned at the time of implantation to sequentially compress the tendon flat on the bone. This tension is retained during subsequent anchor implantation until the entire array is implanted and reduces the chance of creating areas of insufficient compression, bunching, or non-contact.
5. The system has a minimum of four anchors forming each serial array with a single common working suture forming stitches between anchors. In preferred systems a single serial array includes a minimum of 4 and up to 8 anchors. Further, multiple arrays can be implanted in larger or massive tears.
6. Each system includes structure to lock or retain tension in the stitches, either individually as each anchor is placed, or as a set once an array of anchors is implanted that is sufficient to handle loads experienced during normal activity.

The present disclosure includes many types of anchors that can be combined with sutures to form implanted arrays accomplishing the above objectives. Further the anchors and sutures can be arranged in pre-strung arrays for easier implantation with mechanisms or means to tighten, hold and/or lock each suture stitch to create that final stable implanted array that retains tension on each of the suture stitches to hold the tendon in position during movement.

It is recognized in the art that rotator cuff tears are classified into four categories based on tear size and whether a single row or double row repair is completed. Small tears are less than 1 centimeter (cm) in length; medium tears are 1 cm to 3 cm in length; large tears are 3 cm to 5 cm in length and massive tears are greater than 5 cm in length. With prior art devices, surgeons are limited to available large anchors and by the size of the tear as the medial anchors must fit in the tear area that exposes bone. For example, surgeons may use about 1 medial anchor on small tears, 1 or 2 medial anchors on medium tears and 2 or 3 medial anchors on large tears and massive tears. With the high anchor density anatomical repair of the present application, the surgeon is not limited by tear size as the anchors are implanted through the tendon and can use greater than 3 medial anchors on small tears, greater than 5 medial anchors on medium tears, and greater than 6 medial anchors on large tears and massive tears. This can include positioning implants outside the area of a full thickness tear to reinforce areas of partial thickness tears or weaker untorn tendon. For some tears, two rows of anchor may be placed 1-3 cm apart with the present system, if desired. The high-density array of anchors is formed by implantation of the anchors in a chain or row which can be a relatively straight line or curve depending upon the tear to be repaired and the discretion of the surgeon.

One exemplary delivery device system designed for sequential transtendinous implantation of each anchor in the array is disclosed herein as well. The delivery system includes a delivery tool distal portion to be used at the surgical site for implantation of the array, and a proximal portion having a handle and features for managing the anchors and associated sutures and suture lock or other mechanism. The distal portion of the delivery tool includes an anchor delivery tube sized to allow passage of an anchor and associated working suture and suture lock therethrough. The delivery tool is used with a bone punch that is sized as well for passage through the anchor delivery tube. The proximal portion of the delivery tool is configured to allow a physician to introduce an anchor that is pre-strung onto the working suture into the anchor delivery tube. The proximal portion of the delivery tool may include a platform for receiving a magazine carrying a number of cartridges that house the pre-strung anchors individually. The magazine may include a cartridge ejector that allows one cartridge at a time to be removed from the magazine and placed in a slot on the delivery tool. A plunger is used to transfer individual anchors from the cartridge to a lumen at the proximal end of the anchor delivery tube.

In use, the physician places the distal end of the delivery tool at a desired location for introduction of an anchor. Such placement may be performed with the bone punch extending past the distal end of the delivery tool to allow a physician to probe the desired location using the bone punch. The physician then presses the delivery tool distal end against the tendon and applies a force, such as by pounding, against the proximal end of the bone punch to create a path through the tendon and then to create a bone hole. The distal end of the anchor delivery tube, referred to as a nub, may be advanced through the tendon and at least partly into the bone hole as the bone punch is pounded.

The bone punch is then retracted, while the nub is kept in place to maintain registration through the tendon and into the bone hole. With the bone punch retracted, a cartridge is removed from the magazine using the cartridge ejector and transferred to the slot on the proximal portion of the delivery tool, and the plunger is depressed to move an anchor from the cartridge into position for advancement into the anchor delivery lumen. The bone punch is again advanced, this time pressing against the proximal end of the anchor, eventually ejecting the anchor from the anchor delivery tube into the bone hole. As the bone punch pushes the anchor down the anchor delivery tube, the tip of the bone punch can be engaged with a dimple in the anchor, especially if it is a toggle type anchor. If the anchor is a soft anchor, an anchor advancing tool having a slot for receiving the soft anchor may be used rather than the bone punch during advancement of the soft anchor, in some examples.

When the anchor exits the anchor delivery tube within the bone, the anchor must be toggled, oriented or activated so that it is retained in the bone when the working suture is tensioned. Several exemplary anchor types are described below that include differing ways to activate or orient for bone retention. For example, toggle type anchors are rotated (toggled) so their length lays across the punched hole, soft anchors are expanded so they cannot exit the punched hole, and other anchors can include external flanges or other projections that are extended within the bone or bone hole to prevent pullout. The bone punch or anchor advancing tool is advanced so that the tip thereof extends beyond the nub, forcing the anchor into the bone. The bone punch or anchor advancing tool is then retracted into the anchor delivery tube, and the working suture is manipulated to continue orienting or activating the anchor into a preferred retained position. To prevent interference between the anchor and the anchor delivery tube and/or damage to the working suture during orientation of the anchor, the anchor delivery tube may be retracted so that the nub is within the delivery tool. In addition, retracting the anchor delivery tube and/or nub can reduce flossing tension, allowing flossing of the working suture until tensioned and locked. During orienting or activating the anchor, the anchor delivery tube may be pressed against the tendon to prevent or discourage backing out of the anchor and/or fracture of the bone under the applied forces.

In some examples, the first anchor may be affixed to the working suture, and the first anchor omits any locking suture or other means for actively locking the working suture to first anchor. When the first anchor is set in sufficiently strong material inside the bone (which can be harder cancellous bone or may be resting against the under surface of the cortical shell) the delivery device can be set with the punch pin partially extended as it was at the beginning of the procedure and moved for implantation of the next anchor.

With the second and subsequent anchors, both a proximal and a distal suture portions of the working suture extend up through the delivery device. It is recognized that the proximal portion and distal portion of the working suture can be tensioned in some embodiments to aid in rotating and/or seating the anchor in proper position within the bone hole. Prior to such tensioning of the working suture, the nub may be retracted into the outer tube of the delivery tool to prevent interference with or damage to the working suture and/or locking loop (when provided). During setting and orientation of the anchor and subsequent tensioning of the suture, the distal end of an outer tube of the delivery tool may be pressed against the tendon to provide a counterforce against pullout. This is continued until the properly tensioned suture stitch is formed.

This is repeated for a desired number of anchors in the pre-strung chain which is implanted to form a high-density array as described above. As can be understood, the number of suture stitches formed is equal to the number of anchors in the chain implanted minus 1. Further, the string of stitches is serially continuous with each stitch tensioned independently to form a required robust tendon attachment. The continuous string of stitches can form a row or chain of stitches of desired shape. By row or chain, it is meant that the suture stitches extend from one anchor to the next in the sequence of implanted anchors. It is understood that more than one continuous string of stitches can be formed by implanting multiple anchor arrays that together form an overall repair array, especially for large tears.

As previously stated, the distance between ends of a suture stitch (the distance between edges of anchor holes) is preferably less than about 7 mm (less than about 10 mm from center of anchor insertion hole to center of anchor insertion hole) to provide consistent force on the tendon against the bone to reduce creep. One particularly robust array of implanted anchors for rotator cuff repair includes a first array implanted in a medial portion of the original tendon footprint of the supraspinatus and infraspinatus tendons to form a row or line of stitches generally perpendicular to the length or direction of the tendon's forces. A second array can then be implanted laterally nearer the edge of the tear with at least one anchor through the tendon while at least one other anchor is implanted laterally of the tendon edge to reapproximate the tendon properly against the bone. The lateral row can be implanted in a zig zag pattern or other appropriate pattern based on the shape of the tear. Depending upon tear size and location, multiple patterns can be utilized.

As becomes clear in the above description, the pre-strung array of anchors in combination with the working suture and multiple locking sutures creates a strong need for a delivery system that has components that manage the anchors and their attendant sutures or suture sections to maintain orderly implantation, use and sterility during a procedure. Further, the small size of the anchors necessitates some sort of holder or cartridge for individual anchors. Applicants disclose herein an attachable magazine and multi-cartridge assembly that integrates with the above-described delivery device. The assembly includes a cartridge for each anchor in a given array with the individual cartridges stored and managed in a cartridge magazine in a way that maintains the integrity of the array and allows the surgeon to access and use each anchor in the array sequentially.

A first illustrative and non-limiting example takes the form of a method for repairing a torn rotator cuff tendon by reattachment to a humeral head utilizing a seam-like row of serial stitches extending over incremental portions of the tendon between adjacent implanted bone anchors, the method comprising the steps of: providing a pre-strung plurality of anchors including a first anchor, a plurality of intermediate anchors and a final anchor with each anchor having a bone hole insertion diameter of less than or equal to about 3 mm, wherein the first anchor includes a length of working suture affixed thereto, each intermediate anchor having at least one passage therethrough with the length of working suture slidably and serially threaded through the at least one passage of each intermediate anchor and a final anchor also having at least one passage therethrough with the length of working suture slidably threaded therethrough and further including a means for locking the working suture relative to the final anchor; implanting each anchor in a single row through the torn rotator cuff tendon, the anchors each implanted in a bone hole, with the intermediate anchors placed in bone holes formed in the original footprint of the torn rotator cuff tendon with spacing between adjacent anchors a distance of about 10 mm or less as measured from center of bone hole to center of bone hole; applying tension to the working suture after implantation of each intermediate anchor and the final anchor implantation to form a series of single suture tensioned stitches between anchors; and securing the working suture as tensioned to the final anchor with the means for locking the working suture.

Additionally or alternatively, the plurality of intermediate anchors includes six anchors.

Additionally or alternatively, the means for locking the working suture is a locking loop, the locking loop extending adjacent the final anchor wherein the locking loop encircles a portion of the length of the working suture, the locking loop having a first open position allowing the working suture to slide through the locking loop and a second closed position engaging the working suture and preventing sliding of the working suture within the locking loop.

Additionally or alternatively, the means for locking the working suture is a knot tied in the working suture adjacent the passage in the final anchor after tensioning.

Additionally or alternatively, the means for locking the working suture is a one-way slip knot that allows sliding of the working suture in a first direction but prevents sliding in an opposite direction, wherein the step of applying tension to the working suture is performed by pulling the working suture in the first direction.

Additionally or alternatively, the means for locking the working suture is a set of angled projections in the passages of the anchors that allow working suture movement in a first direction but prevent working suture movement in a direction opposite the first direction, and the step of applying tension to the working suture is performed by pulling the working suture in the first direction.

Additionally or alternatively, the means for locking the working suture is mechanical lock that compresses and secures the working suture to the final anchor when activated.

Additionally or alternatively, each intermediate anchor further includes means for locking the working suture thereto.

Another illustrative and non-limiting example takes the form of a method for securing a supraspinatus tendon and an infraspinatus tendon to a humeral head, the method comprising the steps of: providing a first anchor having a length of a working suture secured thereto, the anchor having an insertion diameter in a bone hole of less than or equal to about 3 mm; implanting the first anchor through either of the supraspinatus tendon and the infraspinatus tendon into the humeral head within a medial half of an original combined footprint of attachment of the supraspinatus and infraspinatus tendons to the humeral head; providing a plurality of intermediate anchors, each intermediate anchor slidably received on the length of working suture, each intermediate anchor having a passage therethrough wherein each intermediate anchor is configured for insertion in a bone hole having a diameter of less than or equal to about 3 mm; implanting the intermediate anchors through the tendons into bone holes formed in the humeral head in a serial row within the medial half of the original combined footprint, wherein the first of the intermediate anchors is spaced from the first anchor by a distance of less than or equal to about 10 mm measured from center of bone hole to center of bone hole and each subsequently implanted intermediate anchor is spaced from the just previously implanted adjacent intermediate anchor by a distance of less than about 10 mm measured from center of bone hole to center of bone hole; providing a final anchor, the final anchor slidably received on the length of working suture, the final anchor having a passage therethrough wherein the final anchor is configured for insertion in a bone hole having a diameter of less than or equal to about 3 mm wherein the final anchor further includes means for selectively locking the working suture relative to the final anchor; implanting the final anchor through either of the supraspinatus tendon and the infraspinatus tendon into a bone hole formed in the humeral head within the medial half of the original combined footprint, wherein the final anchor is spaced from the last intermediate anchor by a distance of less than or equal to about 10 mm measured from center of bone hole to center of bone hole; tensioning the working suture at locations along its length to form a stitch extending between each anchor in series to hold the supraspinatus tendon and the infraspinatus tendon against the humeral head; and, securing the tensioned working suture to the final anchor utilizing the means for selective locking to maintain desired tension in the formed individual stitches.

Additionally or alternatively, the plurality of intermediate anchors includes six anchors.

Additionally or alternatively, the means for locking the working suture is a locking loop, the locking loop extending adjacent the final anchor wherein the locking loop encircles a portion of the length of the working suture, the locking loop having a first open position allowing the working suture to slide through the locking loop and a second closed position engaging the working suture and preventing sliding of the working suture within the locking loop.

Additionally or alternatively, the means for locking the working suture is a knot tied in the working suture adjacent the passage in the final anchor after tensioning.

Additionally or alternatively, the means for locking the working suture is a one-way slip knot that allows sliding of the working suture in the a first direction but prevents sliding in a direction opposite the first direction, wherein the step of tensioning the working suture includes pulling the working suture in the first direction.

Additionally or alternatively, the means for locking the working suture is a one way passage that includes angled projections that allow working suture movement in a first direction but prevents moving the working suture movement in a direction opposite the first direction wherein the step of tensioning the working suture includes pulling the working suture in the first direction.

Additionally or alternatively, the means for locking the working suture is mechanical lock that compresses and secures the working suture to the final anchor when activated.

Additionally or alternatively, each intermediate anchor further includes means for locking the working suture thereto.

Another illustrative and non-limiting example takes the form of a method for repairing a torn rotator cuff tendon by reattachment to the humeral head utilizing a seam-like row of serial stitches extending over incremental portions of the tendon between adjacent implanted bone anchors in an original footprint of the tendon on the humeral head, the method comprising the steps of: providing a pre-strung plurality of anchors, including a first anchor, a plurality of intermediate anchors and a final anchor with each anchor having a bone hole insertion diameter of less than or equal to about 3 mm, wherein the first anchor includes a length of working suture affixed thereto, each intermediate anchor having at least one passage therethrough with the length of working suture slidably and serially threaded through the at least one passage of each intermediate anchor and a final anchor also at least one passage therethrough with the length of working suture slidably threaded therethrough and further including a separate locking loop, wherein the separate locking loop encircles a portion of the length of the suture adjacent the final anchor and having a first position allowing the suture to slide through the locking loop and a second position engaging the suture and preventing sliding within the locking loop; implanting the first anchor through the tendon into a bone hole formed in the humeral head within the original footprint; implanting a first of the intermediate anchors of the pre-strung plurality of anchors in a bone hole formed in the original footprint a distance of about 10 mm or less from the first anchor as measured from center of bone hole to center of bone hole, then applying tension to the working suture extending from the first anchor and passing through the first intermediate anchor to form a single suture tensioned stitch between the first anchor and first intermediate anchor; implanting a second of the intermediate anchors in the pre-strung plurality of anchors in the footprint defined by the original insertion of the supraspinatus and infraspinatus tendons a distance of about 10 mm or less from the first intermediate anchor as measured from center of bone hole to center of bone hole, then applying tension to the suture extending from the first intermediate anchor and passing through the second intermediate anchor to form a single suture tensioned stitch between the first and second intermediate anchors; repeating the spacing distances, implanting and tensioning steps for each subsequent serial intermediate anchor and the final anchor; and, activating the locking loop to maintain tension in the created array.

Additionally or alternatively, the plurality of intermediate anchors includes six anchors.

Additionally or alternatively, each intermediate anchor further includes means for locking the working suture thereto.

Additionally or alternatively, at least one intermediate anchor omits any means for locking the working suture thereto.

Another illustrative and non-limiting example takes the form of a method of reattaching a rotator cuff tendon to a humeral head comprising: forming a first bone hole and implanting a first anchor of an anchor system therein, the anchor system comprising: the first anchor; at least one intermediate anchor having an intermediate anchor body with at least one passage therethrough; and a final anchor having a final anchor body with at least one passage therethrough; a working suture secured to the first anchor, passing slidably through the at least one passage of each of the at least one intermediate anchor and through the at least one passage of the final anchor; and a locking means for locking the working suture relative to the final anchor; wherein each of the first anchor, at least one intermediate anchor, and final anchor are configured for placement in bone holes having a diameter of less than or equal to 3 mm; the method further including forming at least one intermediate bone hole and implanting one of the at least one intermediate anchor in the at least one intermediate bone hole; wherein for each intermediate anchor that is implanted the method includes applying tension to the working suture after implanting the intermediate anchor; forming a final bone hole and implanting the final anchor therein; tensioning the working suture after implanting the final anchor; and securing the working suture as tensioned to the final anchor with the means for locking the working suture.

This overview is intended to introduce the subject matter of the present patent application. It is not intended to provide an exclusive or exhaustive explanation. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present invention includes multiple components, devices and methods to create and use an overall system for reattaching soft tissue to bone. It is particularly useful to create a robust repair of torn tendons, such as the supraspinatus tendon, in an arthroscopic rotator cuff repair. The implants and delivery devices make possible a faster, easier and lower failure rate anatomical repair. The tendon is securely attached and held with adequate force to its original footprint with very little creep during movement of the joint. This decreases a patient's time in a sling, increases the rate of healing reattachment of tendon to bone and allows early physical therapy to maintain range of motion and strength.

Figure 1:
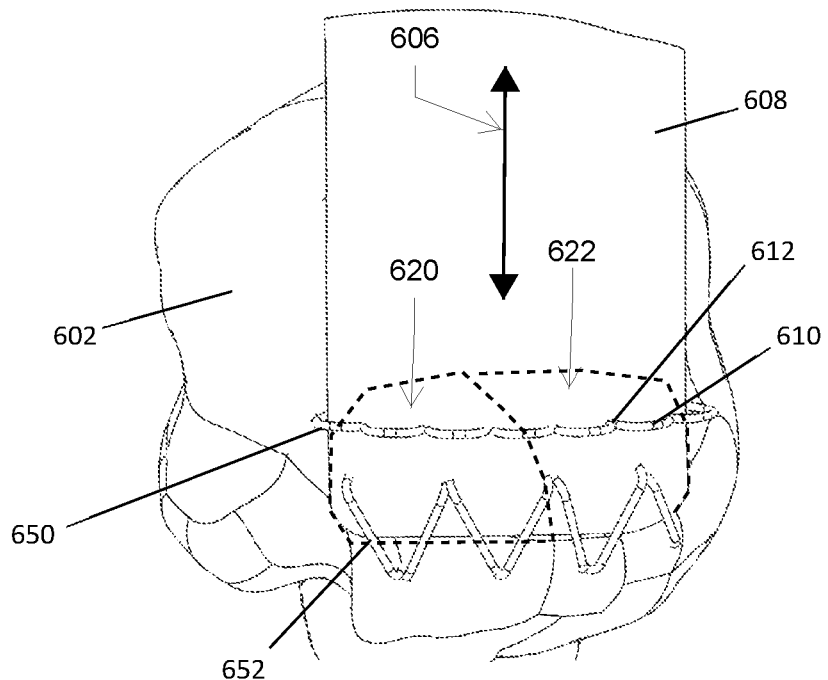
FIG. 1 is an illustration of a representative pattern of continuous tensioned and locked anchor to anchor single suture stitches.

The implanted array of anchors with a continuous set of anchor-to-anchor single suture stitches creates a seam-like attachment akin to a sewing machine construct as illustrated in FIG. 1. FIG. 1 illustrates a rotator cuff tendon 608 attached to the humeral head 602 by a first array of stitches 650. Each stitch includes a suture portion 610 that extend over a portion of the tendon 608 between two adjacent anchors 612. Using the methods and devices disclosed herein can create a row of continuous stitches that are closely spaced, individually tensioned and tightened.

As used herein, the direction of a tendon is the direction in which forces are borne by the tendon for functional use; for example, in the rotator cuff tendon 608 shown in FIG. 1, the functional direction of the tendon can be understood by arrow 606. A preferred pattern includes a row of stitches 650 generally perpendicular to the direction of the tendon as shown in FIG. 1. In a rotator cuff repair these would all be placed in a medial portion of the original tendon footprint, in particular the original tendon footprint of the supraspinatus and the infraspinatus tendons. For illustration, an approximation of the original footprint of the infraspinatus tendon is shown in phantom at 620, and the original footprint of the supraspinatus tendon is shown roughly in phantom at 622; the two footprints may be adjacent one another as shown. In the below described methods, reference may be made to the original combined footprint of the supraspinatus and infraspinatus tendons for convenience. It should also be understood that references below to a first anchor and a final anchor may refer to either end of the row of stitches, as the decision of which end to start with will be up to the physician's judgment or preference in view of patient anatomy.

In some preferred embodiments a second row of anchors 652 is also implanted, especially in a large rotator cuff repair. The second row is implanted laterally of the first row and can include a zig zag pattern to put some anchors in the lateral portion of the original footprint and other anchors lateral of the footprint to hold down edges of the torn tendon. Other configurations are also possible depending on the size and shape of the tear. Anchors may also be placed to create stitches over attached portions of the tendon to reinforce the margins/edges of fully or partially torn tendons.

In some examples, the small cross-sectional size of the anchors (sized for placement in a 3 mm diameter bone hole) allows the anchors to be placed in close proximity to one another (less than about 7 mm between adjacent anchors from edge of bone hole to edge of bone hole). This creates an anchor to anchor suture stitch. Combining this concept with the disclosed anchor design allows the suture stitch to be tightened and locked individually or as a group when the adjacent suture anchors are implanted. This can be repeated many times to implant a row of anchors with continuous independently tensioned and locked stitches between adjacent anchors. Also, because the anchors are in a high-density array, the tension force components on the tensioned suture are more vertically applied to the top surface of the tendon (or other connective tissue) to thereby hold the tendon against the footprint of the bone without creep or slippage during joint movement.

Figure 2A:
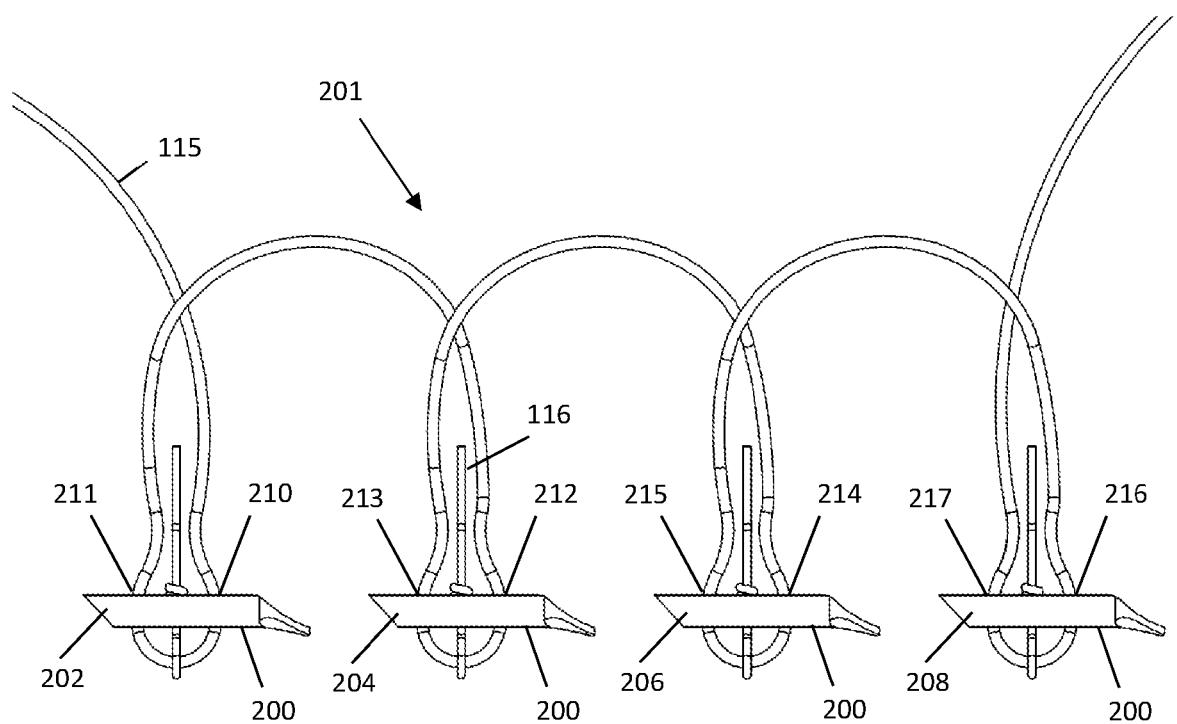
FIG. 2A is an illustration of a pre-threaded array of toggle type anchors.

In some preferred embodiments, individual anchors, as described in detail below, do not function alone. Instead each is part of a pre-strung or stringable array having a common serially disposed working suture therethrough. FIG. 2A illustrates a pre-strung array 201. Each anchor 200 can be implanted sequentially within the array, then the working suture section extending from the just implanted anchor to the just previously implanted anchor can be tensioned. In some embodiments as illustrated FIG. 2A, the working suture is then locked at the just implanted anchor so that a suture stitch between the two anchors provides force against the tendon to hold it in place much like a single sewn stitch.

With the array, multiple stitches can be formed in a continuous array similar to a sewn seam.

In FIG. 2A a pre-strung array 201 of individual anchors 200 is depicted. The anchors 200 may be similar in form and function to the anchor 100 described herein. The shown array has four anchors 200 as a representative chain. It is believed chains of 4 to 12 anchors would be useful in tendon repair procedures such as rotator cuff repair. One particular embodiment includes 8 anchors in an array. As depicted in FIG. 2A, the way in which the working suture 115 is pre-threaded through the series of anchors 200 is important to assure that they will toggle in bone as desired and tension to form the stitch when the suture is tightened. The illustration shows the first anchor 202 to be implanted followed by the second anchor 204, then the third anchor 206 and finally the fourth anchor 208. With this order of implantation understood, the working suture 115 has been pre-threaded down through the top of the proximal hole 210 and back up through the distal hole 211 of the first anchor 202. The working suture 115 then continues to the second anchor 204 where it is threaded down through the proximal hole 212 and back up through the distal hole 213 of the second anchor 204. The working suture 115 then continues to the third anchor 206 where it enters the top of the proximal hole 214 and back up the distal hole 215 of the third anchor 206. The working suture then continues to the fourth anchor 208 where it enters the top of the proximal hole 216 and passes up through the bottom of distal hole 217 of the fourth anchor 208. If the array were more than four anchors, the pre-threading would continue as described for each subsequent anchor.

Figure 2B:
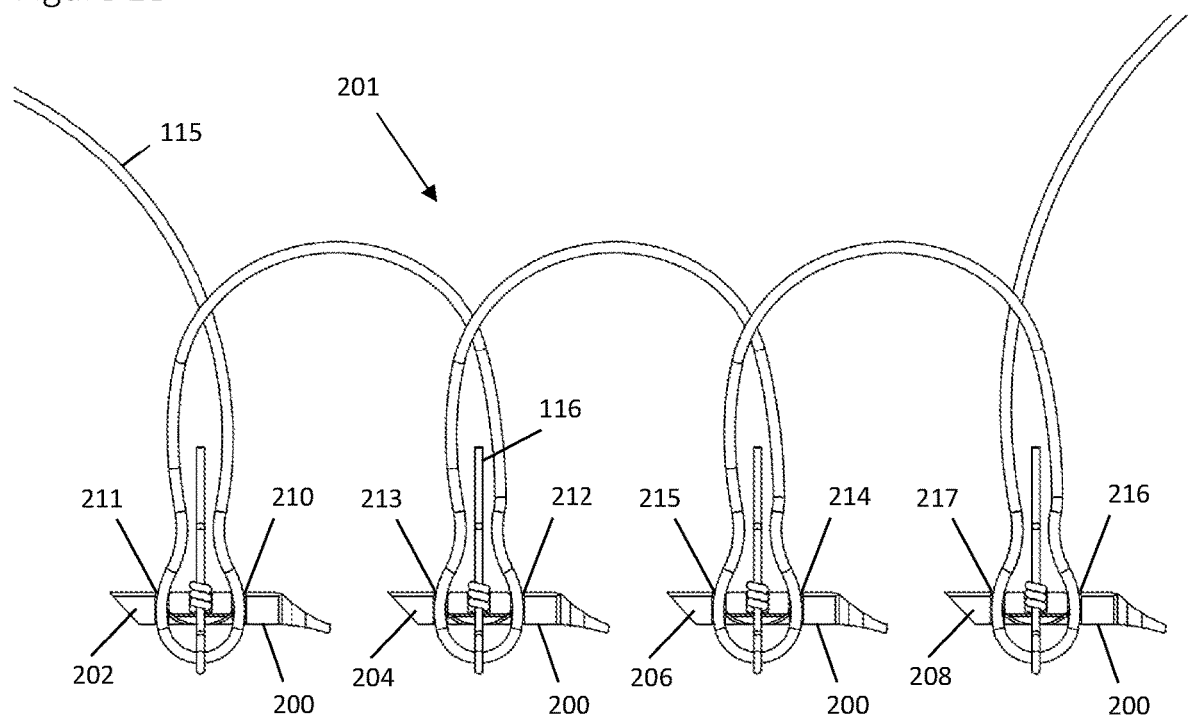
FIG. 2B is an alternative view of FIG. 2A showing the toggle anchors in cross section to illustrate the threading route of the sutures.

FIG. 2B is a cross sectional view of the array of FIG. 2A which more clearly shows the threading of the working suture 115 within the anchors 200 in the array 201. The way in which a locking suture 116 is disposed in the middle passage is also shown for each anchor 200 as described above with each locking loop 118 independent for each anchor. The locking suture 116 can have a preferential point of failure so that it can be tightened then broken off above the slidable knot. This can be accomplished by tying a break knot, or making a nick in, in the free tail of the locking loop just above the slidable knot, as further illustrated in FIGS. 2E to 2H, below. In some preferred embodiments the slidable knot is a 4-throw uni knot and the break knot is in the free tail just above the uni knot. The suture lock may be designed to break at a desired tension with the slidable knot in place sufficient to lock the working suture.

To create an implanted serial array of tensioned and independently locked anchor to anchor suture stitches for attaching a tendon to bone, a surgeon would begin with the pre-strung array 201 described in FIGS. 2A and 2B. The first anchor 202 would be implanted through the tendon into a formed bone hole and the working suture locked. Alternatively, the first anchor 202 can be affixed to the first anchor 202 prior to implantation as this anchor does not have suture pulled through it. The second anchor 204 would then be implanted in close proximity to the first anchor 202, preferably less than 7 mm away (edge of bone hole to edge of bone hole). The second anchor is toggled and the working suture tensioned at the same time by pulling on the working suture 115 that exits the distal hole 213 of the second anchor 204. Tension at this location not only toggles the second anchor 204 but also tightens the working suture 115 going back to the first anchor 202 to form the tensioned stitch holding the tendon against the footprint. The second anchor 204 is then locked so that the stitch remains tensioned and is isolated or independent of other stitches. The process is repeated for the third anchor 206 and fourth anchor 208 or more. In one preferred array, eight anchors are implanted and 7 tensioned and locked stitches in a continuous row are formed. Further, in a rotator cuff repair, multiple arrays can be implanted such as one array extending across the tendon in the medial portion of the footprint and a second array more lateral to the medial position.

As discussed above, one preferred array can include a plurality of anchors, each having a locking loop associated therewith and a common working suture that connects the anchors serially. When the working suture is tensioned between anchors, the working suture segment tightens and forms a stitch that is compressed against the tendon between the anchor ends. Other alternative anchors and array designs are possible to create the same or a similar seam like array of stitches. For example, the first anchor in the array of FIG. 2A includes a locking loop. This loop is not necessary and instead the first anchor in any array could simply have the end of the working suture affixed to anchor in any fashion, such as insertion through a passage on the anchor and affixing with a knot. There is no need to have structure that allows flossing or sliding of the working suture relative to the first anchor in an array.

Figure 2C:
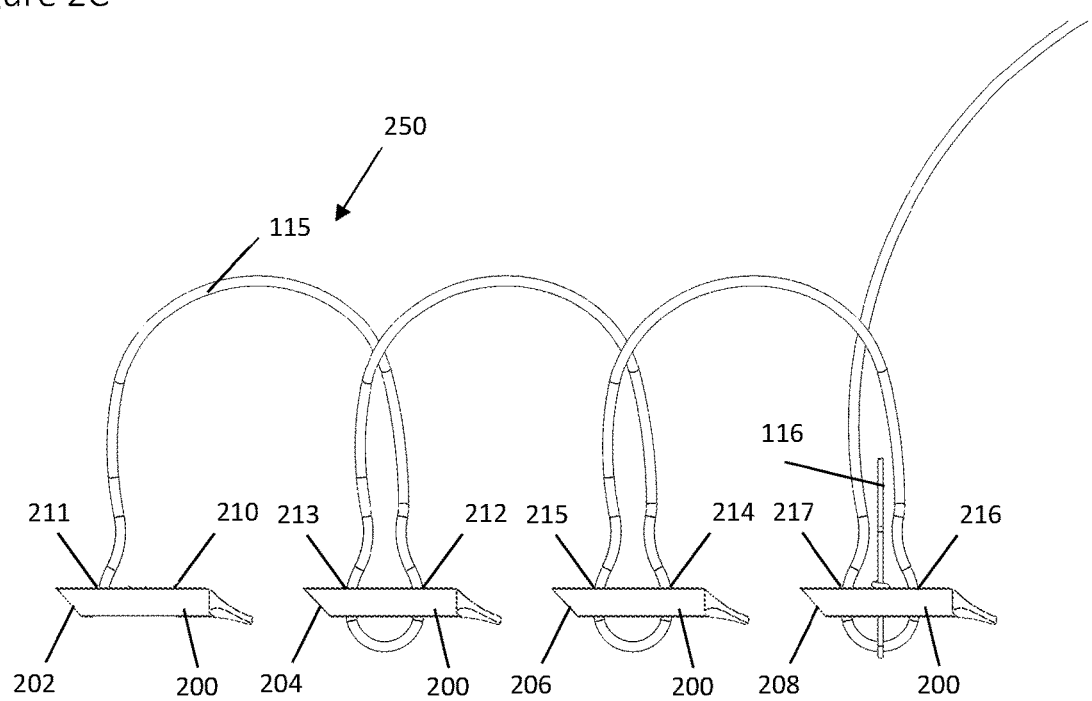
FIG. 2C is an illustration of an alternative array of toggle type anchors.
Figure 2D:
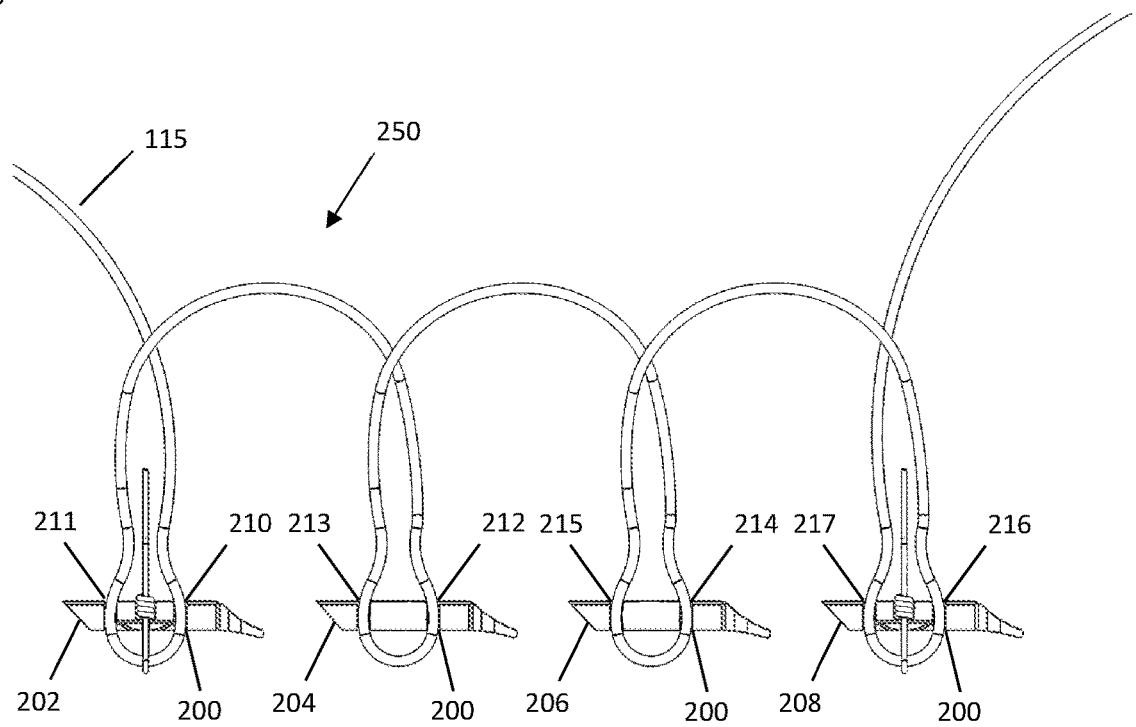
FIG. 2D is an alternative view of FIG. 2C showing the toggle anchors in cross section to illustrate the threading route of the sutures.

Another alternative array is depicted in FIGS. 2C and 2D. The array is similar to the array of anchors of FIGS. 2A and 2B with like parts numbered the same. The distinction is the varied use of locking loops. In some embodiments, not all anchors of the array include locking loops. As stated above, the working suture can be affixed to the first anchor 202 with a knot (or in the alternative, with adhesive, heat attachment, mechanical fixation such as with a screw, or any other suitable attachment), as shown by the working suture 115 only having one end at the first anchor 202, with no locking suture on the first anchor 202. It may be observed that the working suture 115 terminates at a distal portion of the first anchor 202, which may be useful for aiding in toggling the first anchor 202. In this example, one or more of the intermediate anchors 204, 206 in the array may simply have the working suture 115 threaded through the passages in the anchor so that it can be flossed through the anchor as needed to tension the working suture 115 (and also to aid in toggling each anchor). However, as depicted the last anchor 208 in the array does include a locking loop 116 to affix the working suture relative to the last anchor after it is tensioned. It is recognized that in some embodiments none of the intermediate anchors include locking loops while in others some of the intermediate anchors can include locking loops. In some preferred embodiments, the working suture and anchor passage, along with the tortuous path followed by the working suture (such as highlighted in FIG. 3C, below) provide sufficient friction so that the working suture can be tensioned after each anchor implantation and the tension is retained under conditions during surgery where the tendon is not being flexed and loaded/unloaded as during live use. Therefore, the array can be implanted as discussed with respect to FIGS. 2A and 2B with each stitch tensioned after each intermediate anchor implantation, but without a locking suture 116 or other locking structure to secure the working suture at each intermediate anchor 204/206. The last anchor is then implanted, the working suture tensioned and the locking loop associated with the last anchor is activated. The locking of the working suture on the last anchor essentially locks the entire array in tension so that the implanted array can be exposed to the loads of shoulder movement as needed during healing and rehabilitation. That is, in some examples, only the last anchor of the array may have the locking loop 116.

FIGS. 2E-2H are a series of illustrations of an exemplary toggle body type anchor showing a single working suture slidably disposed in passages through the anchor and through a locking loop. As discussed above, in some anchors the locking loop is omitted such as in the first anchor which can have the working suture affixed thereto or some intermediate anchors that rely on the last anchor suture lock to hold the array in tension. The locking loop is configured to have an open position allowing movement of the single working suture, and a closed or locked position that prevents movement of the single working suture. In the illustrative example shown in FIGS. 2E to 2H, the free end 121 of the suture lock 116 is configured to break away from the locking loop 118 proximal of the sliding knot 120. A break knot is illustrated at 122 and is one example of a way of introducing weakness in the suture lock. The break knot 122 is located a distance above the sliding knot 120, sufficient that when the suture lock 116 breaks away, the sliding knot 120 remains intact and secure. For example, the break knot 122 may be about 3 to 10 mm proximal of the sliding knot, or more or less. Rather than a break knot 122, a nick, crimp, or other point of weakness may be imparted at the desired or preferential point of failure in the suture lock 116.

Figure 2E:
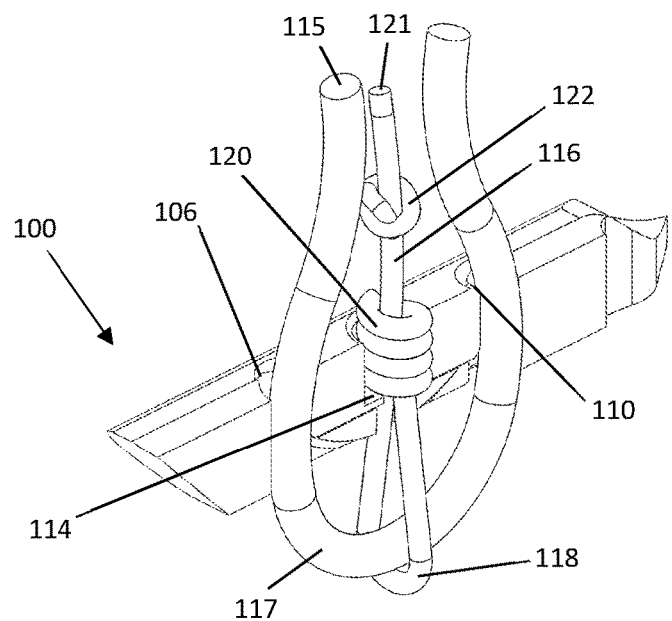
FIG. 2E is partial cut-away view of a toggle body with a working suture and locking suture in an open position illustrated.
Figure 2F:
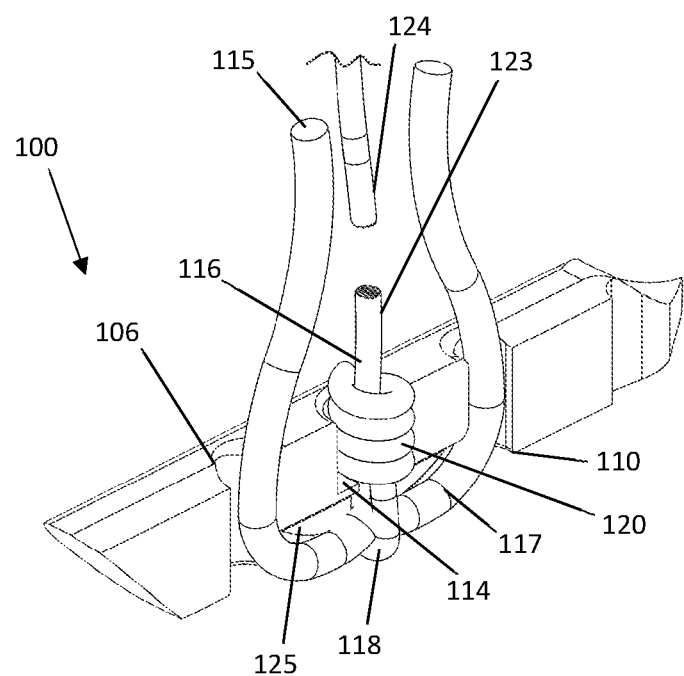
FIG. 2F is partial cut-away view of the toggle body of FIG. 2E having a working suture and locking suture in a closed position illustrated.
Figure 2G:
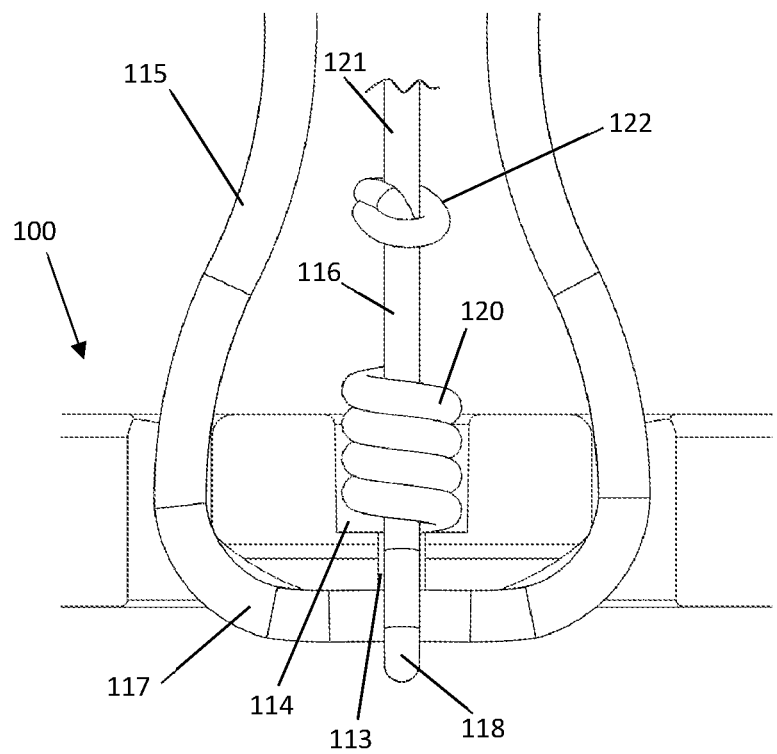
FIG. 2G is a schematic illustration of the interaction between the locking suture and the working suture.
Figure 2H:
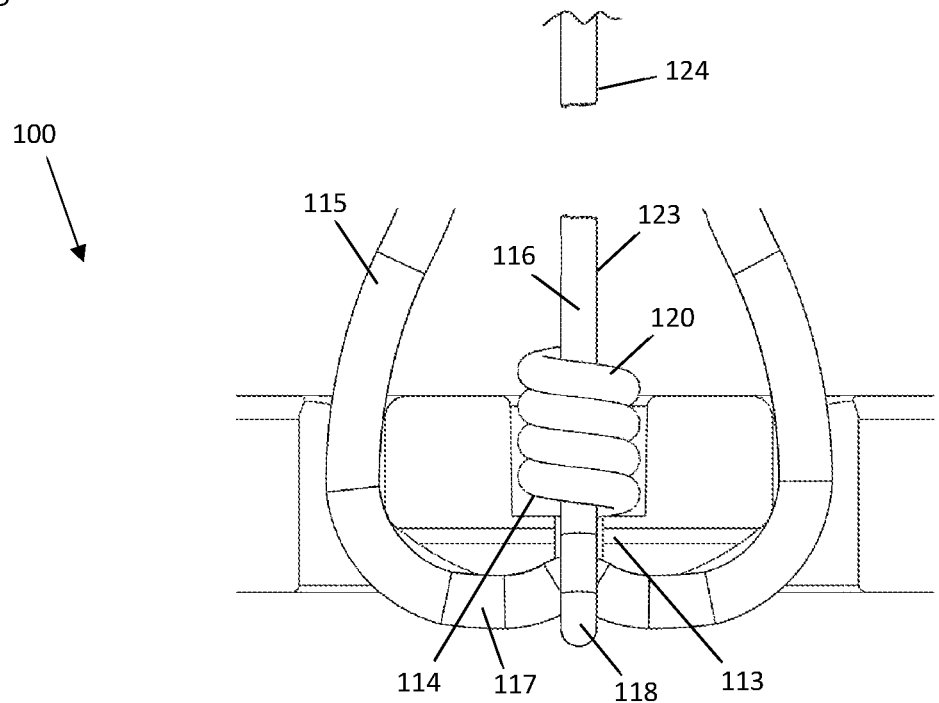
FIG. 2H is a schematic illustration of an alternative interaction between the locking suture and the working suture.

FIGS. 2G and 2H depict the way in which the locking loop 118 pulls the section 117 of the working suture 115 into the oval portion 113 in two different embodiments. The degree to which the section 117 of the working suture 115 enters the slot 113 will be dependent upon how tight the loop is closed, the size of the locking suture and the size of the slotted opening. In preferred embodiments, at least a portion of the cross section of the working suture 115 is pulled into the slot so that the edge surfaces of the slot walls provide significant friction and aid in locking. In another example, the preferential point of failure is designed to allow the locking loop 118 to be drawn into the slot before the failure occurs.

The locking loop 118 in combination with the design of the middle passage 108 is an assembly for locking a slidable working suture 115 when tensioned in a suture toggle body 100 during tissue fixation to bone. The locking loop 118 encircles a portion of the working suture 115, wherein collapsing the locking loop 118 compresses the cross section of the working suture 115 to lock the working suture 115 when tensioned. The suture lock 116 is preferably formed of a suture having at least a slidable knot 120 tied therein to form the loop 118 to allow collapsing of the loop 118 when a tightening leg 121 through the second passage 108 is tensioned. The second passage 108 has an upper portion for receiving the slidable knot 120 at least partially therein that terminates in a platform 114 within the toggle body 100 that does not allow passage of the slidable knot. The second passage includes a lower portion having an oval shape for allowing both legs of the locking loop to pass therethrough side by side and out the passage. A particularly preferred knot is a 4-throw uni knot. However, other slidable knots 120 may be used, as desired. Further, the second passage oval portion is sized to allow at least a portion of the working suture 115 to be pulled therein in response to tension on the locking cord. The working suture 115 is preferably a braided multistrand suture having a compressible cross-sectional area that reduces by at least about 25% when the locking loop is tightened during use. The working suture 115 can be a round and/or braided No. 2 suture in some embodiments. Other size, shape and/or configuration sutures may be used.

As also shown in FIGS. 2F and 2H, after the sliding knot 120 is tightened, and the working suture is drawn at least partly into the slot, the preferential point of failure in the locking loop 116 (such as the break knot or nick described above) breaks, leaving free tail at 123 on the locking loop, a distance above the sliding knot, while the rest of the proximal portion of the suture lock 124 can be discarded. In some examples, a more proximal portion of the suture lock is secured to a cartridge, so that a physician may cause the suture lock to break as shown by pulling on the cartridge itself, as further described below. In an example, the preferential point of failure is designed to allow tightening of the locking loop 118 onto the working suture 115, and/or drawing of the working suture into the slot on the bottom of the anchor before the failure occurs. For example, the locking loop and the preferential point of failure may be configured for breaking under a pull strength in the range of 3-10 pounds of force, more preferably, 5-7 pounds of force, or more or less as desired. The pull strength needed to tighten the locking loop 118 onto the working suture may be less than the pull strength needed for breaking the preferential point of failure in some examples by, for example, an amount in the range of 0.5 to 3 pounds, or 0.75 to 2 pounds, or about 1 pound.

Figure 3A:
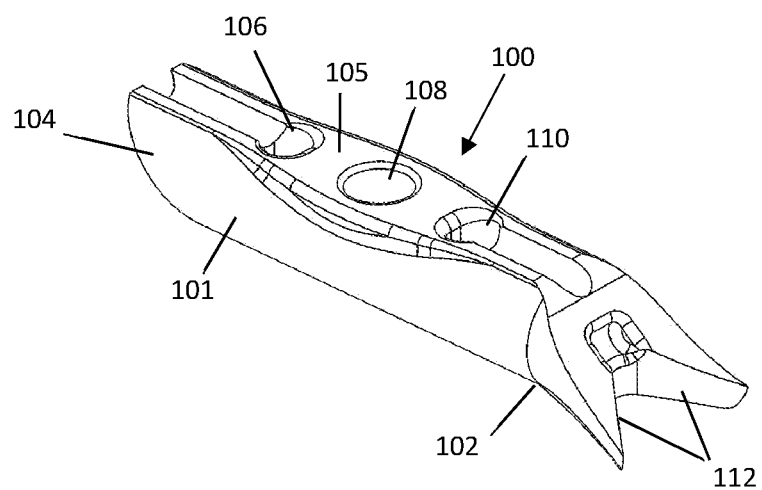
FIGS. 3A-3C are perspective views of a representative toggle body anchor.

Referring to FIG. 3A, a perspective view of a representative anchor in the form of a toggle body 100 is illustrated. The toggle body 100 can be an elongate body 101 having a length defined by a proximal end 102 and a distal end 104. The elongate body 101 can be a generally cylindrical body but other shapes are possible. For example, as shown in FIG. 2A, the toggle body 100 is generally cylindrical but the top surface 105 and bottom surface 107 have flat axially-extending surfaces that allow room for sutures when the toggle body 100 is in a round delivery tube. The length of the toggle body 100 is substantially longer than the diameter thereof, allowing the toggle body 100 to be inserted lengthwise or axially into a small bone hole. Once inserted, unlike most anchors used today, the entire body is pivoted or toggled so that it stays within the bone and has substantially its entire length compressed against material inside the bone. That is, the longitudinal axis of the toggle body 100 is rotated or pivoted from the direction used to insert through the bone hole, thereby preventing removal. This approach means that removal would require the anchor itself to fail, rather than simply being released from surrounding tissue, and provides high pullout strength (greater than 600 N before anchor failure when implanted in the array disclosed herein) from an anchor requiring a very small insertion hole (less than about 3 mm). As previously stated and described in detail below, small insertion holes allow much closer placement of anchors in a high-density array.

The toggle body 100 can have a length of about 6 mm to about 10 mm in some embodiments. This length gives adequate strength while leaving enough room inside the bone for the high number of anchors implanted. The toggle bodies are preferably molded or machined from a polymeric material, preferably a high tensile strength material such a poly-ether-ether ketone (PEEK) which is highly biocompatible. In applications where MRI imaging would not be an issue, metal can be utilized in part or all of the toggle body.

Figure 3B:
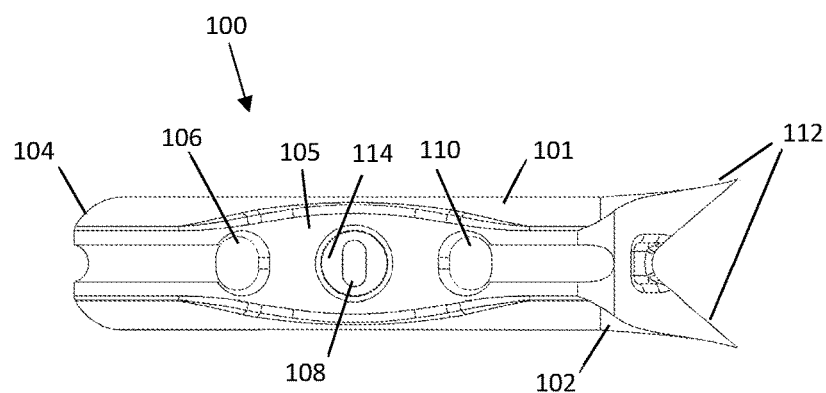

Referring now also to FIGS. 3B (top view) and 3C (bottom view), it can be seen that the toggle body 100 can include a number of holes or passages through the cross section of the toggle body 100. As illustrated, the toggle body 100 has a proximal bore or passage 110, a middle passage 108 and a distal passage 106. The passages 106, 108, 110 extend from the top surface 105 to the bottom surface 107 such that the passages 106, 108, 110 extend through the cross section of the elongate body 101. In other embodiments, the toggle body may have fewer or more bores or passages, such as having a single bore, two bores, or more than three bores. In the illustrated embodiment, the proximal passage 110 and distal passage 106 receive a portion of a common working suture slidable with respect to the toggle body 100 during use. The middle passage 108 receives a locking suture which is independent for each anchor used in an array of anchors.

The distal end 104 of the toggle body 100 has an angled surface. As shown, the angled surface creates a longer upper longitudinal surface 105 than lower longitudinal surface 107. In other words, the upper surface projects a greater distance distally than the lower surface. This is useful during insertion of the toggle body 100 because the projecting distal surface plows into cancellous spongy bone when implanted to initiate at least partial rotation of the toggle body during insertion. Keeping in mind that the present toggle bodies 100 are preferably implanted through the tendon, it is important that the toggle body 100 toggle every time or it may pull out of the bone hole under tension yet not be visible as it will be under the tendon.

The proximal end 102 of the toggle body 100 can include one or more projecting fins 112. The illustrated embodiment includes two fins 112. Each fin 112 projects outward and proximally. Further, in some embodiments, as depicted, the fins 112 project downward as they extend proximally. The bone hole in which the implant will be placed is sized to closely match the general diameter of the toggle body. In contrast, as shown, the fins 112 each project laterally beyond the outer cross section or diameter of the elongate body. During insertion the fins 112 flex inward under compressive force due to contact with the inner diameter of a delivery tube to fit in the bone hole.

Once delivered and released from compressive forces of the delivery tube, the fins 112 relax to a size greater than the bone hole. In some preferred embodiments, each fin tip extends about an additional 0.5 mm beyond the size of the bone hole where that feature is inserted. Such fin tips may also be described as extending about 0.5 mm beyond the maximum outer diameter of the rest of the anchor body, for example, in the range of 0.4 mm to 0.7 mm. This feature provides an added safeguard against the toggle body 100 backing out of the bone hole under tension if the toggle body 100 has not adequately toggled. Further, the fins 112 are positioned so that tension on the toggle body 100 causes the partially toggled anchor to grab cancellous bone and further rotate the anchor.

Figure 3C:
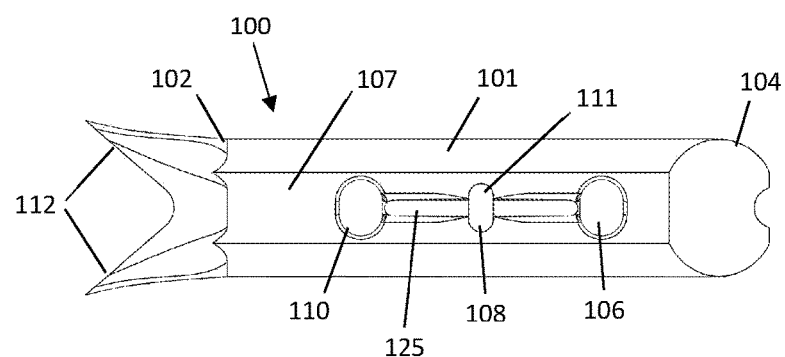

The top and bottom views of FIGS. 3B and 3C show details of the proximal 110, middle 108 and distal 106 passages. In particular, the middle hole has a platform 114 formed within the elongate body 101, part way through the cross section. That is, in this example, the middle passage 108 has a change in size or shape partway along its length, to define a platform 114. From the bottom view, it can be seen that the middle passage 108 continues from the platform 114 with a slotted or oval shape or portion 111, while having a circular profile from the top view. The function of these passages is detailed in the cross-section perspective views of FIGS. 2E and 2F wherein representative cords or sutures 115, 116 have been pre-strung on the toggle body 100.

First, there is a single suture, called herein the working suture 115 that extends into the proximal passage 110 from the top surface, and extends out at the bottom surface. The working suture 115 then extends up through the distal passage 106 from the bottom surface and out through the top surface. This leaves a section 117 of the working suture 115 extending past or adjacent the middle passage 108 along the bottom surface. The working suture 115 can be flossed or is slidable through the distal 106 and proximal passage 110, meaning the toggle body 100 can slide on the working suture 115 when tension is applied. Second there is a locking loop 118 that encircles a portion of the section 117 of the working suture 115 extending adjacent the outer surface of the toggle body 100 between the proximal 110 and distal 106 passages. The locking loop 118 has a first open position as depicted in FIG. 2E wherein the working suture 115 is free to slide through the locking loop 118 and a second closed position depicted in FIG. 2F wherein the locking loop 118 engages the section 117 and prevents it from sliding within the locking loop 118.

Several examples refer to a suture, cord, or thread, which can be used as the working suture 115 or in the locking loop 118. These elements may be, for example, made of natural material such as silk and/or synthetic materials such as polyglycolic acid, polylactic acid, and polydioxanone, each of which are known for use as absorbable sutures, and/or nylon and polypropylene, which are typically non-absorbable. Various coatings, including antimicrobial, anti-wicking or lubricious coatings may be applied as well. More broadly, these elements 115, 118 may include any item that can be used to couple together objects in a surgical environment, such as any sufficiently biocompatible metal, natural material, plastic or other artificial material adapted for use in a surgical procedure. Monofilaments or more complex structures including braids, weaves, windings, twisted threads, coated or multilayer member, etc. may be used.

In the embodiment depicted, the locking loop 118 extends from the bottom surface of the toggle body 100 through the middle passage 108. The locking loop 118 includes a cord or suture having at least a slidable knot 120 tied therein to allow collapsing of the locking loop 118 when a free end or proximal end 121 of the suture lock 116 extending through the middle passage 108 is tensioned. As shown, the upper portion of the middle passage 108 is sized to receive at least a portion of the slidable knot 120 therein. The slidable knot 120 then contacts the surface of the platform 114 which does not allow the knot to pass through towards the bottom opening. The lower oval portion 113 of the middle passage 108 is a slot or oval which allows both legs of the locking loop 118 to pass therethrough, preferable side by side in the slot direction. The interaction of these components locks the working suture 115 with respect to the toggle body 100.

As shown, especially seen in FIG. 3C, the bottom of the toggle body 100 includes a channel 125 formed in the bottom surface 107 between the proximal 110 and distal 106 passage. When the working suture 115 is tensioned, it is pulled up into this channel 125 which is sized to make the suture less able to floss or move therethrough by increasing frictional resistance to such movement, but does not lock the suture. Further, the working suture then has two near 90-degree angle turns at the bottom openings of the distal 106 and proximal 110 passage which also make it more difficult to floss, but do not lock the working suture 115. The locking loop 118 closing around the working suture 115 and pulling it toward and at least partially into the slot or oval portion 113 is the structure that locks the suture so that cumulative friction prevents slippage of the working suture 115.

The above discussion of arrays, anchors and the working suture forming stitches as implanted focuses on the use of one particular anchor type, the toggle body. This is one preferred anchor design, however it should be recognized that the method of creating a seam like attachment akin to a sewing machine construct can be practiced with any type of suture anchor provided it meets the necessary criteria of being implantable in a bone hole having a diameter of less than or equal to about 3 mm, and can accommodate a working suture therethrough that allows flossing and tensioning of the working suture to form individual tensioned stitches. Further, the first anchor must have the ability to lock the working suture thereto or be supplied with the working suture affixed as by a knot, and at least the last anchor in the array must have a locking loop or other means for affixing the working suture to the last anchor after tensioning. The locking or affixing of the suture to the first and last anchors at a minimum maintains the stitches in the array in tension against the tendon which is against the bone in healing contact. Intermediate anchors may include, or may omit structures or locking loops for locking the working suture thereto.

Figure 4A:
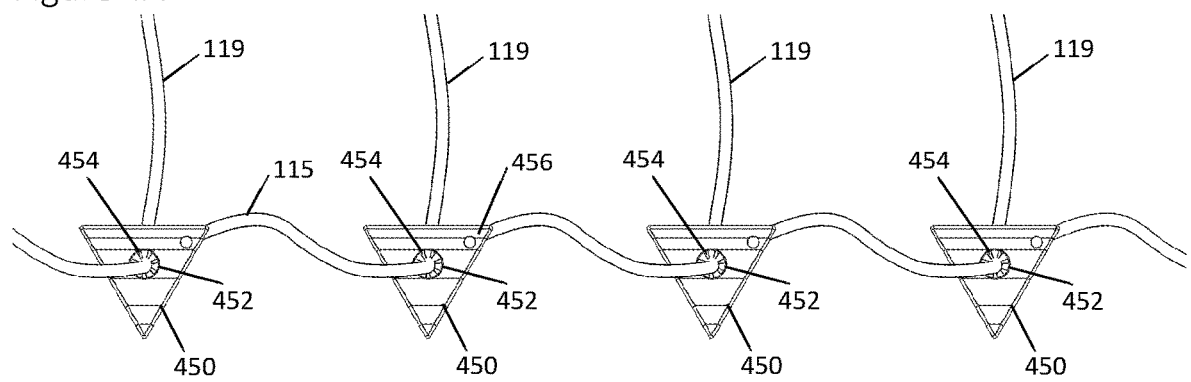
FIG. 4A illustrates an alternative array of wedge like anchors joined by unidirectional tensionable sutures.
Figure 4B:
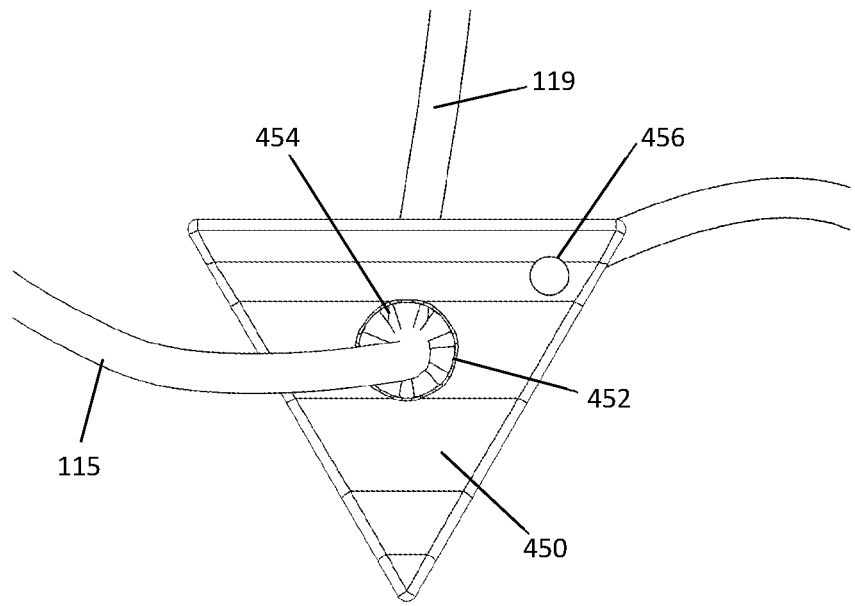
FIG. 4B illustrates in further detail an anchor of the array of FIG. 4A having a one-way suture passage therethrough.

Referring now to FIGS. 4A and 4B, one alternative anchor design and array that can be used in accord with the method of the current application is depicted. First, the anchors 450 are of a wedge shape design. Any wedge shape design, as known in the art can be utilized. For implantation the anchors can be sized smaller in one dimension for insertion then rotate like a toggle type anchor for locking in the bone. Alternatively, the anchors can be rolled within a tubular member for insertion into a bone hole where upon insertion the wedge unrolls to the depicted shape and locks within the bone.

As also depicted in FIG. 4A and in more detail in FIG. 4B each anchor can include a passage 452 therethrough for slidably receiving the working suture 115. In the depicted embodiment each anchor 450 is show with a plurality of barbs 454 or protrusions projecting inwardly toward the center of each anchor passage 450. With this feature the working suture 115 becomes slidable in one direction as the barbs are preferably angled to bend in that direction while the working suture can not floss in the opposite direction due the barbs digging into or frictionally engaging the working suture. The array can be implanted as discussed with other embodiments, however, tensioning of the stitch is accomplished by pulling the working suture 115 extending from each anchor in the first direction and the tension is maintained due to the lock accomplished by the barbs 454 or protrusions in the passage. This type of one-way passive lock can be incorporated in any anchors of the present invention if desired. In the example shown, a single working suture 115 may be used. Alternatively, there may be several individual segments of working suture 115, each having a first end permanently affixed to one anchor (see affixing location 456), passing through the passage 452 of the subsequent anchor, with a free tail 119 extending therefrom. To tension an anchor to anchor stitch, the free tail 119 of the working suture 115 can be pulled. If, instead, a single working suture is used, the free tails 119 and the affixing location 456 would be omitted, and the suture 115 would simply run from one anchor to another. In some examples, the first anchor 450 may include the affixing location 456 or may otherwise be permanently secured to the working suture 1115. In some examples, the last anchor in the series of anchors may have an additional locking structure associated therewith, such as a locking loop as shown in other examples.

Figure 5A:
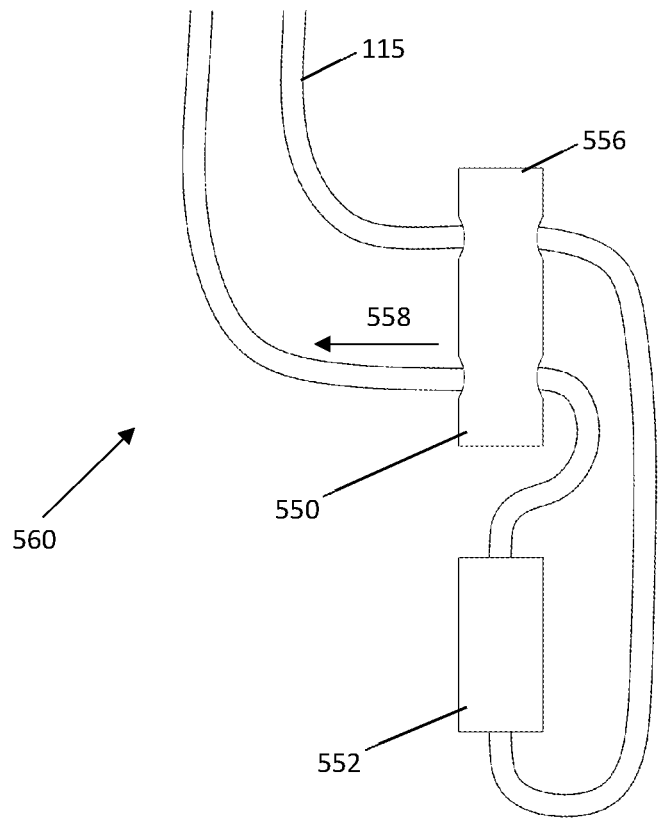
FIG. 5A illustrates another alternative anchor incorporating a toggle body with a separate one-way suture passing member.
Figure 5B:
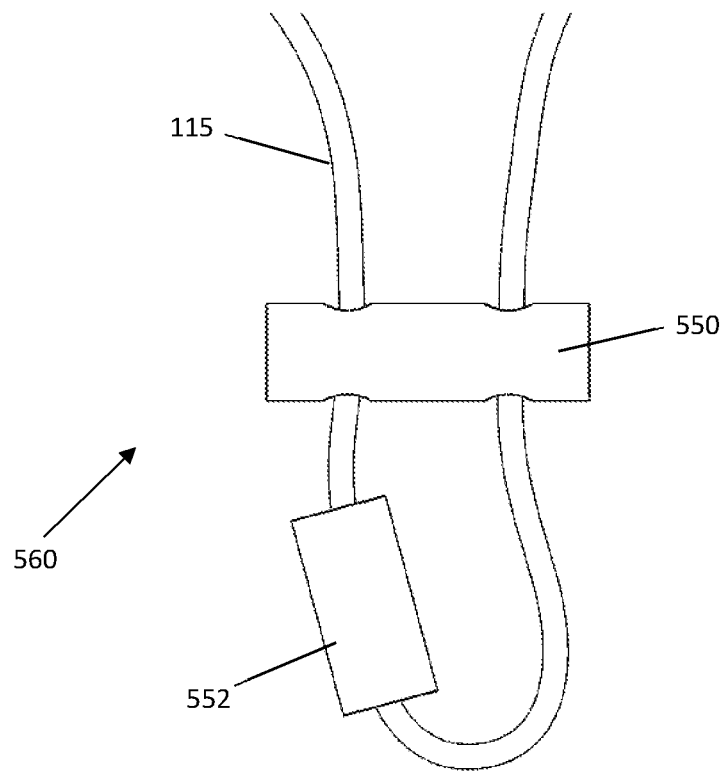
FIG. 5B further illustrates the anchor FIG. 5A in its orientation on implantation in bone.
Figure 5C:
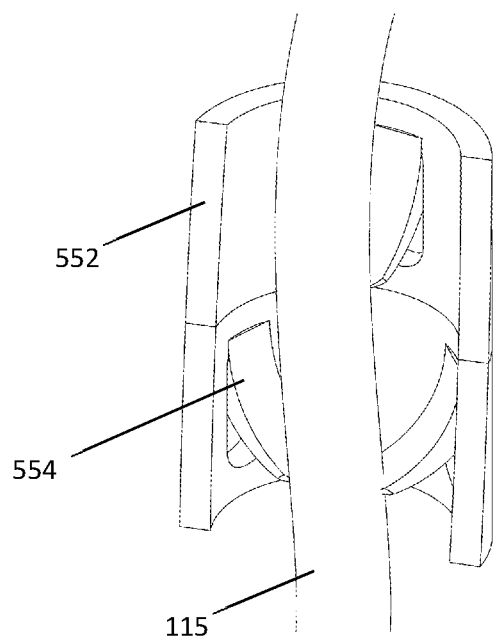
FIG. 5C provides a cross section view of the one-way locking mechanism within the separate suture passing member of FIG. 5A.

Next referring to FIGS. 5A to 5C, another alternative anchor design is depicted. This exemplary design is a two-piece toggle anchor 560 which includes a toggle body 550 and a separate passive one-way suture locking member 552. The toggle body 550 can be of similar design to previously discussed toggle type anchors, however the working suture of this embodiment passes through one passage of the toggle body 550, then passes through the suture locking member 552 before going back through the toggle body 550. With this two-piece design, the toggle body and anchor locking member can be made with a less than or equal to 3 mm insertion diameter. The toggle body 550 and suture locking member 552 may be aligned lengthwise end to end for insertion in a bone hole. As depicted in FIG. 5B, after implantation in bone, the toggle body can be rotated and pulling on the working suture tails will also cause the anchor locking member to be pulled up against the longitudinal side of the toggle body 550. Although not shown, the toggle body 550 may include fins (similar to fins 112 shown in FIG. 3A) at a proximal end thereof 556, if desired, to limit back-out as the anchor is toggled. The toggle body 550 may be toggled by pulling on the more distally passing portion of the working suture, as indicated by direction arrow 558.

The anchor locking member 552 depicted is preferable a passive suture locking member as described for the wedge type anchors of FIG. 4A. The working suture passes though a passage in the locking member and can slide relative thereto, however, as best shown in FIG. 5C, the locking member includes internal radial projections that are preferable angle longitudinally and allow the suture to slide one direction while frictionally engaging or digging into the projections in the other direction. It is recognized that the same function could be accomplished with smooth internal surfaces and using a working suture that has projections or barbs, however, this alternative is not preferred due to the need for the working suture to pass through and extend over tendon tissue in forming the seam like row of stitches preferred herein, as any such barbs or projections may damage the tendon as the working suture 115 is tensioned.

Figure 6A:
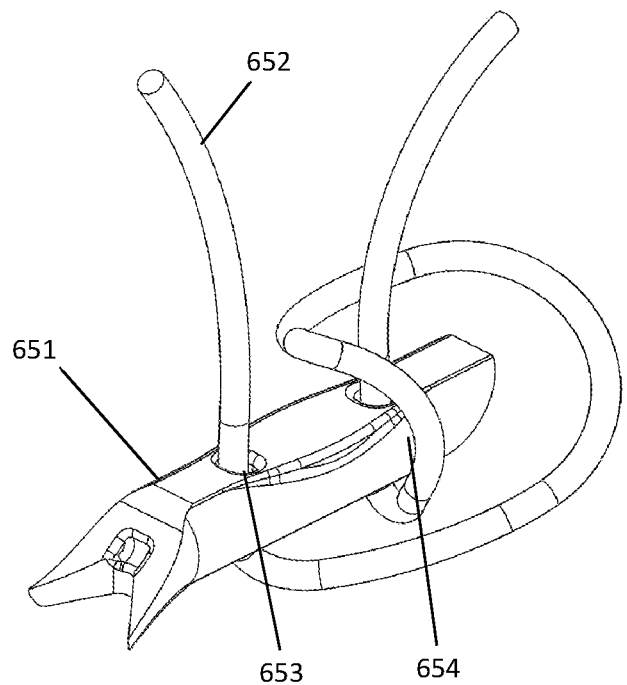
FIG. 6A-6B illustrate another alternative anchor that can be used in an alternative array incorporating a one-way slip knot.
Figure 6B:
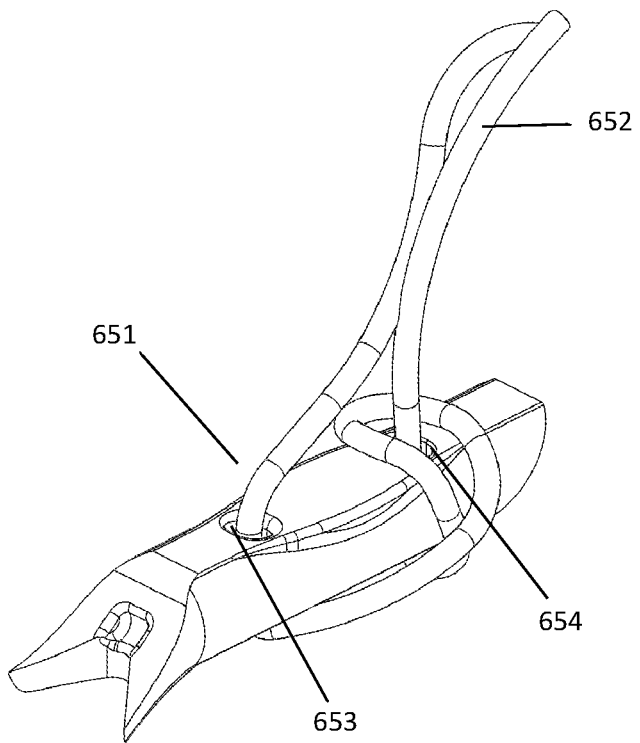

Another alternative embodiment of a toggle body and suture arrangement is depicted in FIGS. 6A and 6B. As can be seen in the drawings, the toggle body 651 is the same design as the toggle body 200 (having two bores), described above. In this embodiment the working suture 652 is the routed through the passages 653, 654 to create a one-way knot. The toggle body 651 includes a second hole 654 through the elongated toggle body extending from the first longitudinal surface to the second longitudinal surface at a spaced interval along the elongated toggle body 651 relative to a first hole 653. The working suture 652 exits the first hole 653 at the second longitudinal surface and wraps around the elongated toggle body and around a portion of the working suture extending from the second hole 654 at the first longitudinal surface of the toggle body 651, then into the second hole through the second longitudinal surface and out the first longitudinal surface. This forms a one-way locking knot preventing the suture from sliding or increasing friction in one direction but allowing sliding in the other direction. Although not depicted, a locking loop could also encircle the working suture 652. This anchor design could be included in any of the previously disclosed arrays to achieve the method of forming a seam like repair of anchor to anchor tensioned stitches, and may be used as a first, last, or intermediate toggle body, as desired.

Figure 7A:
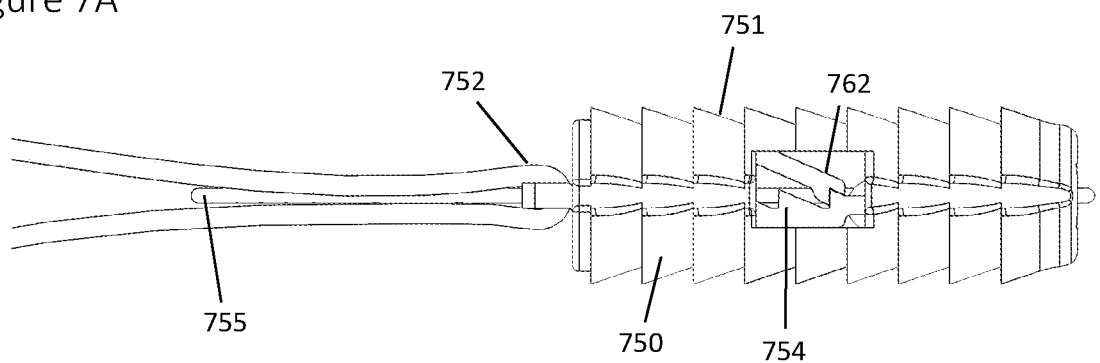
FIG. 7A-7B illustrate another alternative anchor incorporating external retention flanges and an internal mechanical suture locking mechanism.
Figure 7B:
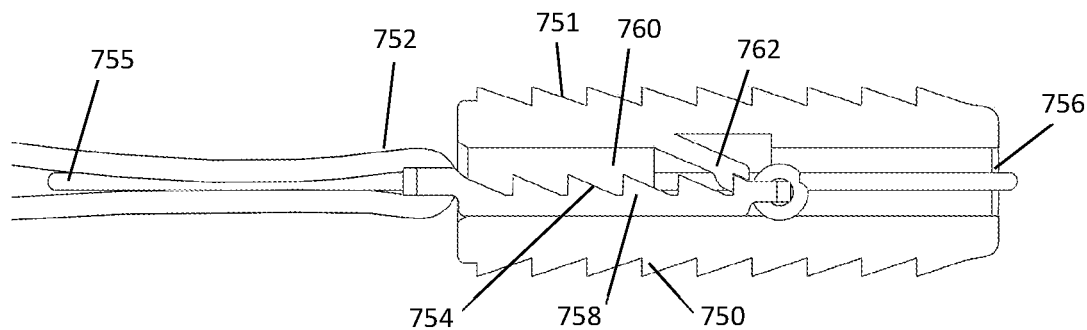

Next referring to FIGS. 7A and 7B, another suture anchor 750 is depicted that can be utilized in methods of forming a seam like array of tensioned stitches. The anchor 750 includes a cylindrical exterior have flanges 751 projecting therefrom for retention of the anchor when inserted in a bone hole. Further, the working suture 752 passes through an opening at a proximal end of the anchor 750, and can be flossed through the opening, relative to the anchor. With flossing, the anchor could be used as an intermediate anchor in an array. However, the anchor in FIG. 7A is also depicted to include a locking member 754 that can affix the working suture relative to the anchor 750. As detailed in cross-section in FIG. 7B, the locking member 754 includes a pull suture 755 that extends into the internal core of the anchor and to the distal end where it wraps around a shoulder 756, before extending back proximally to attach to a locking arm 758. The working suture passage is at the proximal end of the locking arm 758. As illustrated, pulling on the pull suture 750 will draw the locking arm 758 distally into an anchor passage 760. The teeth of the locking arm 758 engage with a pawl 762 as the locking arm 758 advances into the anchor passage 760. This movement pulls the locking suture in crimped fashion into the anchor body passage 760 and locks it therein. This type of locking anchor could be utilized in any of the disclosed arrays previously discussed.

Figure 8A:
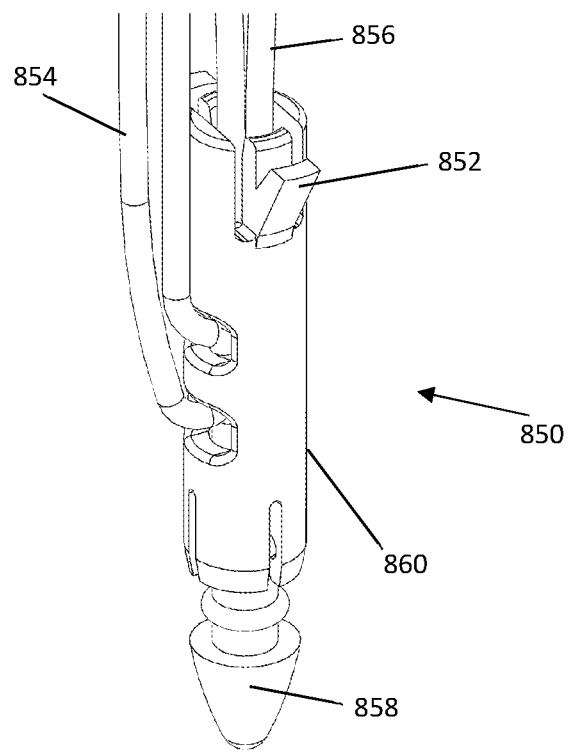
FIGS. 8A-8B illustrate another alternative anchor having activatable external legs for anchor retention in bone and an internal active suture locking mechanism.
Figure 8B:
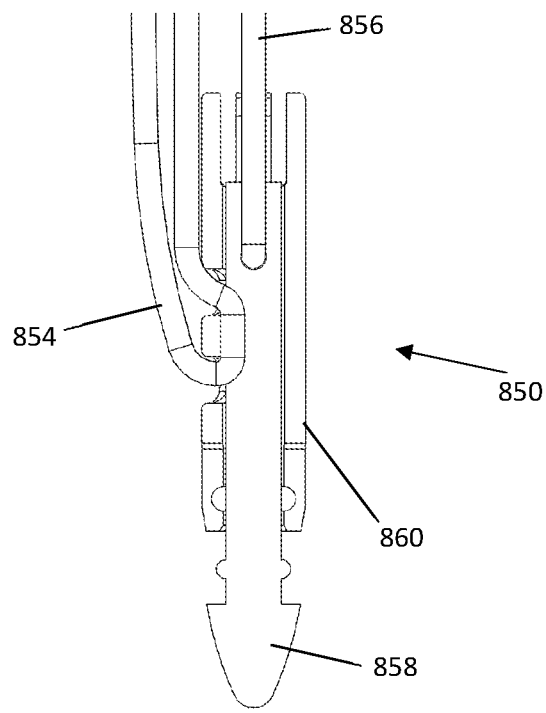

Next referring to FIGS. 8A and 8B, another alternative suture anchor 850 is illustrated. In this example, retention of the anchor 850 in a bone hole is accomplished with retention arms 852 that are expanded after the anchor is inserted in the bone hole. The anchor 860 includes an outer tubular body 860 that has an internal body 858 slidably disposed therein. The internal body 858 can be moved from a first distally extending position to a more proximal position and locked therein. Retention arms 852 on the outer tubular body 860 say in a reduced diameter state as they are introduced, and allow one-way movement down into the bone hold. The application of a force to withdraw the retention arms 852 causes each to catch on the surrounding bone, holding the anchor 850 in the bone hole. This prevents back-out as the working suture 854 is flossed to tighten the preceding stitch. It may be noted that the retention arms 852 occupy two sides of the outer body, allowing the working suture 854 to pass by unimpeded. As flossing is completed, a force is then applied to the locking suture 856 to draw the inner body in an upward direction relative to the bone hole. When the internal body 858 is moved in this way shoulders on the internal body further secure the retention arms 852 in a radially expanded position to lock the anchor in bone. As can be seen in FIG. 8B, movement of the internal body 858 in a proximal direction, as the suture lock 856 is pulled, causes the working suture 854 to be pulled into the outer tubular body and pinched in locking arrangement between the internal wall of the outer tubular body and the internal body. Protrusions shown on the distal portion of the inner body snap into detents in the outer body to secure the lock. This type of anchor could be utilized in any of the disclosed arrays previously discussed.

Figure 9A:
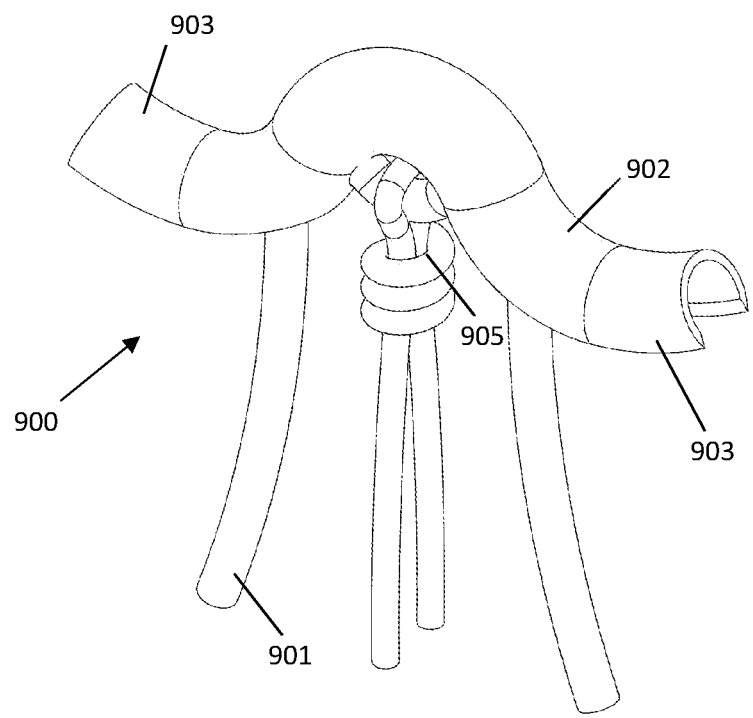
FIGS. 9A-9B illustrate features of a soft suture anchor that can be utilized in an implant array.
Figure 9B:
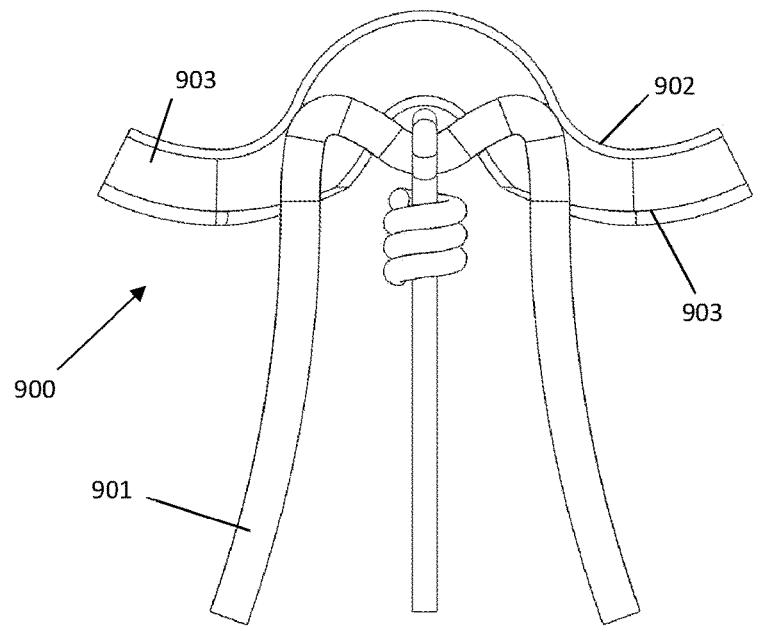

FIGS. 9A and 9B illustrate an exemplary all-suture anchor that can be used alone or incorporate a locking suture or locking loop configuration relative to the working suture and anchor member. The illustrations also show a single working suture slidably disposed in passages through the anchor member and through a locking loop. The locking loop is configured to have an open position allowing movement of the single working suture, and a closed or locked position that prevents movement of the single working suture relative to the anchor member and/or the locking loop. In some embodiments the locking loop is omitted as was done with other intermediate anchors described above.

Referring to FIG. 9A, a simplified perspective view of a representative soft anchor 900 is illustrated. The anchor 900 includes two components, namely a working suture 901 that is slidably disposed within the lumen of an anchor member 902. The anchor member 902 as illustrated can be a length of hollow woven suture material. As depicted the ends 903 of the anchor member 902 flare outward away from the working suture. The anchor member 902 is a soft or flexible member that can easily fold into a linear configuration for insertion in a small bone hole. After insertion, the tails of the working suture 901 can be tensioned which causes the anchor member to migrate toward the bone hole opening. However, the designed ends 903 extending laterally when relaxed will catch on the bone hole and cause the anchor member 902 to expand radially and be locked within the bone hole.

In some examples, the ends 903 of the anchor member 902 are open on one side, as depicted in the figures, while a central portion of the anchor member 902 forms a complete cylinder and is not open on any side thereof, thereby maintaining the anchor member 902 on the working suture 901 while allowing the ends 903 to flare outward as shown. In some examples, the entire anchor member 902 is a soft and/or flexible material. In other examples the ends 903 may have an additional coating or different structure that adds rigidity to the ends and/or central portion of the anchor member 902. In still another example, the anchor member can be generally stiffer throughout, at least relative to the working suture 901, to provide additional anchoring strength. For example, the anchor member 902 may be formed of a different type of suture or with a different thickness of suture than the working suture 901. The anchor member 902 may be, for example, a coated, braided synthetic material having greater stiffness and larger outer diameter, and the working suture may be a relatively thinner, braided (for knot security) natural material of relatively lesser outer diameter. Other combinations may be used, as desired. In an example, the anchor member 902 may be formed of a hollow braid, cut to length, slit to form the ends 903, and then coated to prevent fraying along the ends, if desired.

FIG. 9B shows the anchor of FIG. 9A as implanted and expanded within a bone hole. Tails of the working suture 902 extend from the bone hole for attachment to tendon. At the same time, the projections or flanges 903 of the anchor member 902 are trapped and secured within the bone. In this secured configuration, the working suture 901 is still slidable or flossable relative to the anchor member. A slidable working suture 901 may allow tensioning of individual suture stitches that extend from one anchor to the next anchor in the serial row of the array. Anchors of this exemplary design can be incorporated into previously disclosed exemplary arrays on a working suture. Once emplaced in the bone hole and with the working suture 901 tensioned to form a stitch, a locking loop 905 can be pulled (similar to other examples having a locking loop) to securely hold the working suture 901 in a fixed position relative to the locking loop and the anchor member 902. A number of additional example soft anchor may be found in U.S. Prov. Pat. App. No. 63/231,143, filed Aug. 9, 2021, titled TENSIONABLE AND LOCKABLE SOFT SUTURE ANCHORS AND ANCHOR ARRAYS FOR ANATOMICAL ATTACHMENT OF SOFT TISSUE TO BONE, the disclosure of which is incorporated herein by reference.

In some examples a toggle anchor may also include a movable locking structure associated with the toggle body itself. The locking structure in such examples may be a means for locking a working suture, in addition to the various examples shown above. Some illustrative examples are shown in U.S. Prov. Pat. App. No. 63/231,136, filed Aug. 9, 2021, titled TENSIONABLE AND LOCKABLE MICRO SUTURE ANCHORS AND ANCHOR ARRAYS FOR ANATOMICAL ATTACHMENT OF SOFT TISSUE TO BONE, the disclosure of which is incorporated herein by reference.

In some examples, a series of anchors disposed on a single working suture may have multiple different designs. For example, a first anchor may be any of the above designs, but may be unique within the series of anchors in that it is permanently affixed to the working suture. A set of intermediate anchors can then follow, with each intermediate anchor having the same design. A last anchor may have a third design within the array, with the last anchor having a locking loop or other structure to actively secure the working suture once the entire array has been implanted and tensioned. In another example, an array may include a first anchor that is affixed to a working suture, a second anchor that includes an active locking structure, several intermediate anchors lacking a locking structure or only having a passive locking structure, and two final anchors each having an active locking structure, or any other suitable combination of anchors that do not lock the working suture, or which passively lock the workings suture with anchors that actively lock the working suture. Illustrative arrays may include any combination of the above anchors, as desired.

Figure 10A:
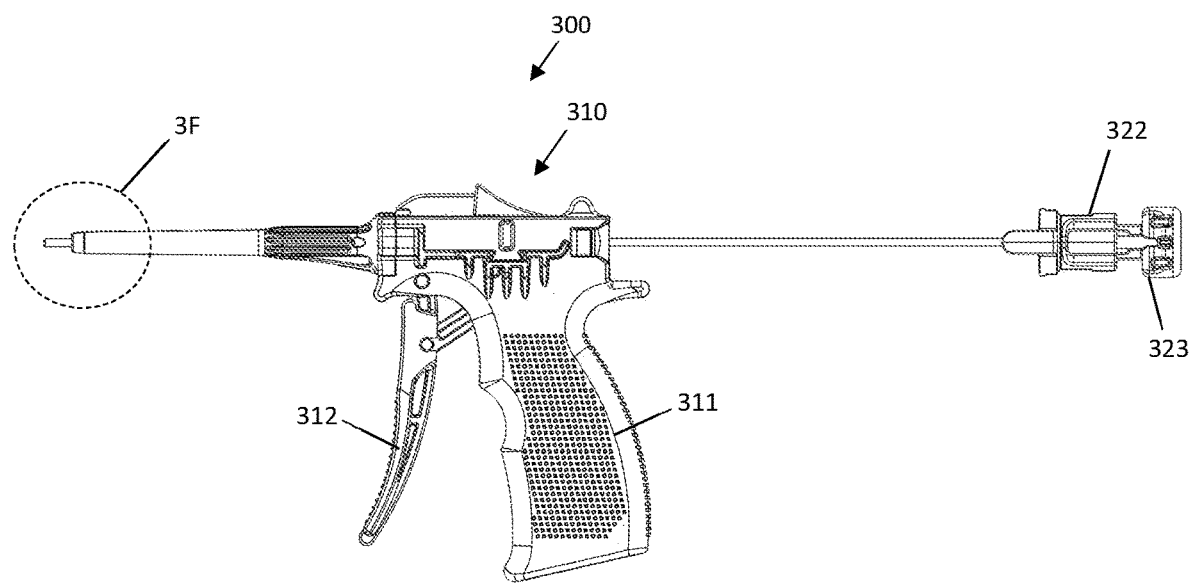
FIG. 10A is a perspective view of an example anchor delivery device.

One preferred anchor delivery device 300 for transtendinous implantation of individual anchors in an array is depicted in FIG. 10A. The delivery device 300 is particularly useful to implant anchors disclosed above but especially useful and described in detail with respect to toggle type anchors and arrays as depicted in FIGS. 2A-2H.

Figure 10B:
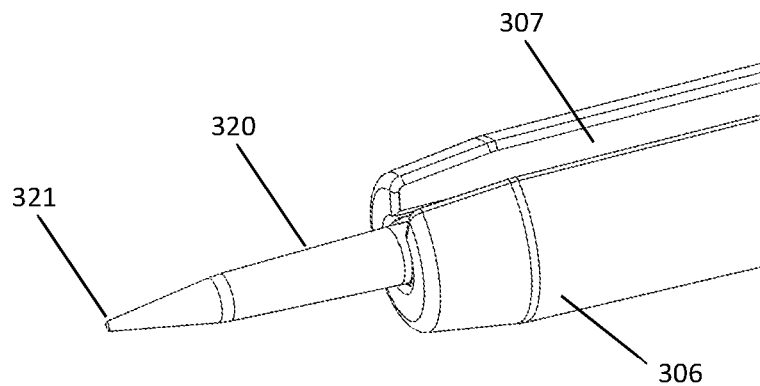
FIGS. 10B-10D are close up views of the distal end of the anchor delivery device of FIG. 10A in various set configurations.
Figure 10C:
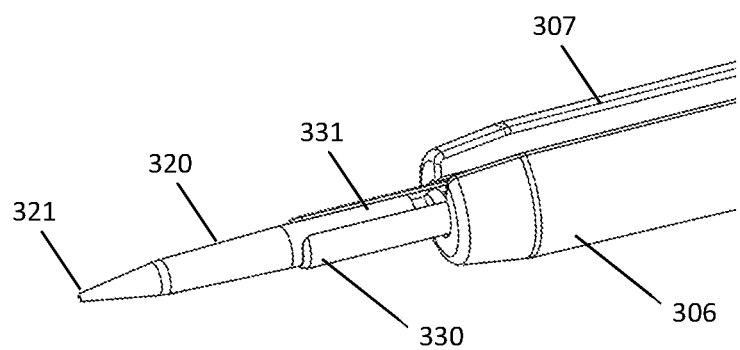
Figure 10D:
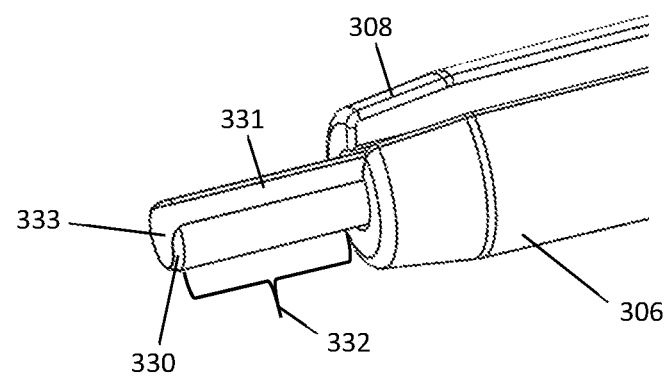

FIG. 10A is a perspective view of an example anchor delivery device in one exemplary configuration, and FIGS. 10B-10D are close up views of the distal end of the anchor delivery device corresponding to FIG. 10A in varied useful configurations. Starting with FIG. 10A, the delivery device 300 can be a gun-like component that has a proximal housing 310 that includes a pistol grip type handle 311 and trigger 312 that moves from a spring retained released position to an engaged position upon squeezing and holding the trigger (as further illustrated below). The trigger 312 is linked to moveable internal features within the proximal housing 310 to provide desired functions during implantation described below. The delivery device 300 includes an elongate tube 306 extending distally from the proximal housing 310. The elongate tube 306 includes a longitudinal slot 307 over its length for receiving sutures therethrough as anchors are passed through the central lumen of the tube.

FIG. 10A also shows that the proximal housing 310 is associated with a bone punch having a distal punch head 322 and a proximal punch head 323. The proximal punch head 323 has a tapping surface 324 at its proximal side. Combined elements 322 and 323 form a punch head assembly. As illustrated in FIG. 10B, the bone punch also includes a punch pin 320 having a tapered point 321 adapted for probing through the tendon and/or grabbing the tendon to aid positioning. Positioning may include positioning the tendon in its original footprint, for tendons that are detached. In some examples, positioning as a separate step may be omitted or limited, such as when repairing a partial tear, such as a partial thickness articular side tear or combination of full thickness and articular partial thickness tears. A tendon can be considered positioned at a location for securing to bone either by virtue of having placed a fully torn or detached tendon at a location, such as its original footprint, where it can be re-attached, or, with a partial tear, when the tendon is located where a physician desires to have it when applying anchors to repair or otherwise address the partial tear.

The punch pin 320 and tip are configured for being pounded into bone to create a bone hole. The tapered tip 321 is also used in some methods disclosed herein to engage and push against the proximal end of an anchor. The punch pin 320 extends through the proximal housing 310 and the elongate tube 306. The punch pin 320 is affixed to the proximal punch head 323 and is slidable within the distal punch head 322. The distal punch head 322 snap latches to the proximal housing 310 of the delivery device. The proximal punch head 323 and distal punch head 322 are connected by a spring-loaded mechanism that holds the punch pin 320 in a fully extended position when the proximal punch head 323 is pushed against the distal punch head 322 and latched. When the proximal punch head 323 is released from close connection with the distal punch head 322, the spring loading causes the punch pin 320 to withdraw proximally to a partially retracted position with only a short distal portion of the punch pin 320 extending beyond the elongate tube 306 for use in probing a potential implant site (as shown in FIG. 10B, for example).

FIG. 10C shows another configuration of the delivery device 300. The action of latching together the proximal punch head 323 with the distal punch head 322, with the distal punch head 322 engaged with the proximal housing 310, advances the anchor delivery tube 330 distally, and forces a distal portion (referred to as a nub, 332 as highlighted in FIG. 10D) of the anchor delivery tube 330 past the distal end of the elongate tube 306. The anchor delivery tube 330 also has a longitudinal slot 331 aligned with the longitudinal slot 307 of the elongate tube for passing a suture therethrough. The fully extended configuration shown in FIG. 10C may be achieved as the surgeon begins tapping or pounding on the proximal punch head 323, causing the proximal and distal punch heads 322, 323 to latch together on the proximal housing.

FIG. 10D shows a next configuration of the delivery device. Here, the distal punch head 322 is no longer engaged with the proximal housing 310, and the proximal and distal punch heads 323, 322, are not latched together. The disengagement of the distal punch head 322 and housing 310, and disengagement of the proximal and distal punch heads 323, 322, is caused by actuation of the trigger 312. As described in the method illustration of FIGS. 12A-12G, below, this configuration would arise after a bone hole is created, and is used to introduce an anchor/suture into the anchor delivery tube for implant. To facilitate such a step in the procedure, a portion of the anchor delivery tube 330 referred to as the nub 332 remains extended from the distal end of the elongate tube 306. With the bone punch retracted or removed, the anchor delivery tube 330 now defines an open lumen 333 to allow an anchor to be introduced and passed therethrough with the aid of the reinserted bone punch, as detailed below. As also highlighted in FIG. 10D, optionally, the distal end of the elongate tube 306 may be tapered as shown at 308. The taper 308, in some examples, provides the elongate tube 306 with a blunt distal tip that can be used to maintain force against the outside of a tendon during manipulation of an anchor and/or tensioning of a stitch between two anchors.

At a high level, the procedure may be understood as follows. With the anchor delivery device 300 in the configuration shown in FIG. 10B, the physician may probe the surgical site to identify a location where an anchor is to be implanted. Once the desired location is identified, the physician applies force to the tapping surface 324 of the bone punch to force the bone punch through the tendon and to create a bone hole using the distal tip 321 of the punch pin 320. As the physician advances the bone punch in this manner, the proximal and distal punch heads 323, 322 will become latched together to form the configuration as shown in FIG. 10C. The same action of advancing the bone punch relative to the elongate tube also advances the anchor delivery tube 330 and nub 332 beyond the distal end of the elongate tube 306. Next, the trigger 312 is actuated to release the bone punch 320, pulling the bone punch 320 in a proximal direction to create the configuration as shown in FIG. 10D. The implant tool 300 is held in position, using the nub 332 to maintain registration with the formed bone hole. In some examples, a portion of the nub 332 will be inserted into the bone hole.

An anchor is then introduced into the anchor delivery tube 330 and passed down the lumen 333 thereof to the distal end, with force applied to advance the anchor using the bone punch assembly. Complete insertion of the anchor can be confirmed by maintaining pressure against the tendon to hold the nub 332 in the desired registration relative to the bone hole, and pushing the proximal punch head 323 in the distal direction until the distal punch head 322 latches with the proximal housing 310 and the proximal punch head 323 latches with the distal punch head 322. Now the trigger 312 will again be actuated, however, due to mechanisms within the housing, this second actuation of the trigger after insertion of the anchor will apply positive retraction force, along with spring force, to retract the anchor delivery tube 330 and nub 332 into the distal end of the elongate tube 306, as well as retracting the bone punch.

With the nub retracted, the physician can manipulate toggling of the anchor using the working suture without the nub 332 possibly damaging the working suture, while force can be maintained against the tendon and bone by pressing the distal tip of the elongated tube 306 against the tendon. After toggling the anchor, the delivery tool 300 is pulled back from the implant position and the suture lock is secured by pulling on the suture lock cord. If the anchor is the second or a subsequent anchor in a series, the physician may tighten the working suture to form a stitch while keeping pressure against the tendon with the elongated tube 306 prior to moving the delivery device to a next position. The delivery device is then reset and the configuration of FIG. 10B is again assumed.

The above procedure may be modified for insertion of a soft suture anchor by, for example, removing the bone punch and inserting into the anchor delivery lumen an anchor delivery tool. The anchor delivery tool may have a slot, for example, for holding such a soft anchor, as disclosed in U.S. Prov. Pat. App. No. 63/231,143, filed Aug. 9, 2021, titled TENSIONABLE AND LOCKABLE SOFT SUTURE ANCHORS AND ANCHOR ARRAYS FOR ANATOMICAL ATTACHMENT OF SOFT TISSUE TO BONE the disclosure of which is incorporated herein by reference.

Figure 11A:
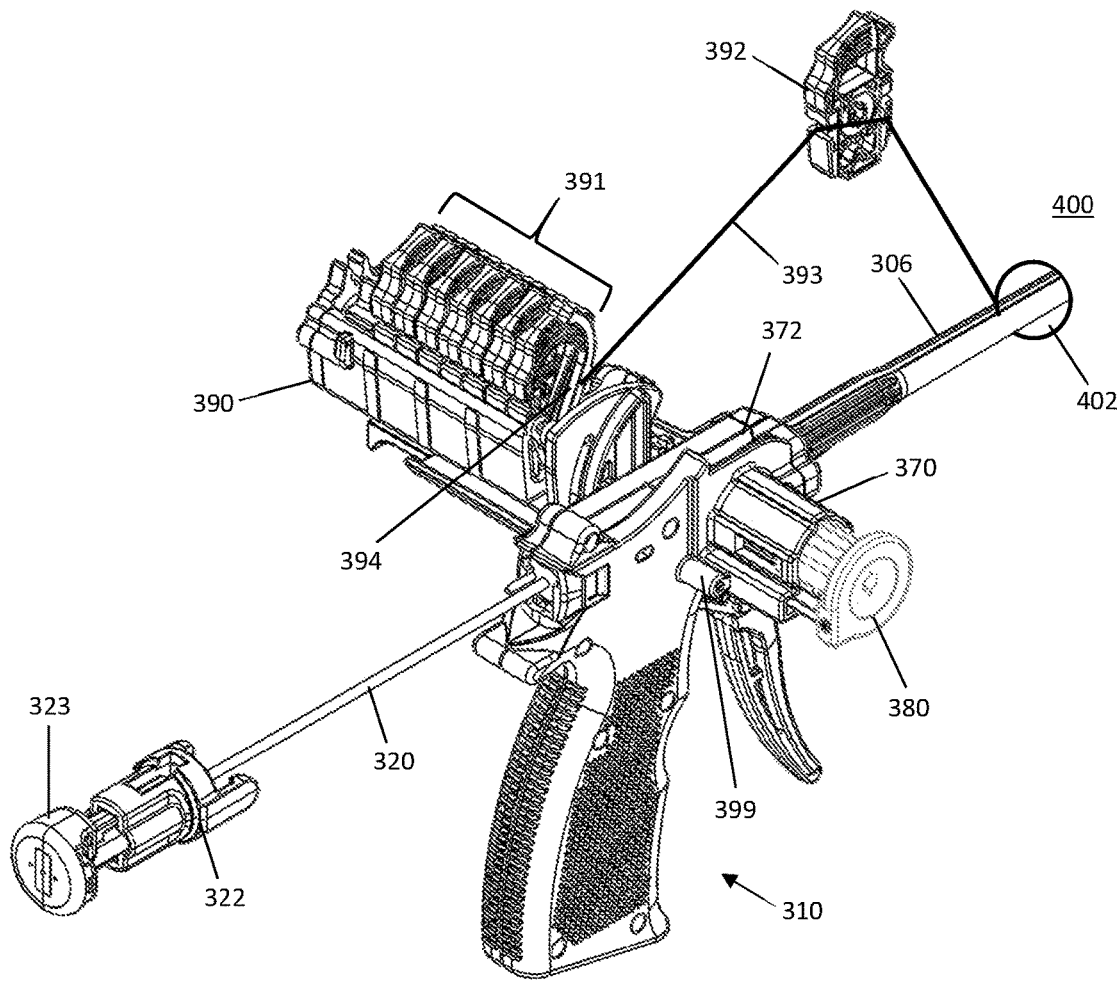
FIG. 11A is a partial perspective view of an alternative anchor delivery device illustrating the bone punch, anchor cartridges and magazine and plunger for anchor loading.
Figure 11B:
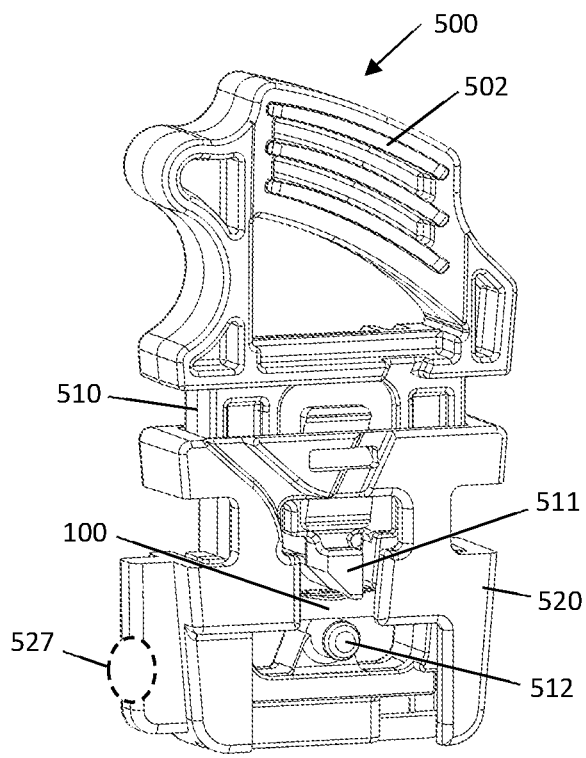
FIGS. 11B-11E illustrate a cartridge for holding a toggle anchor.

Referring now to FIG. 11A, another embodiment of a delivery device is illustrated. The device of FIG. 11A features a plunger for delivering anchors from individual cartridges 391 to the delivery device and a magazine 390 for holding cartridges on the anchor delivery device. The delivery device is generally shown at 300 with the proximal housing at 310. On one side of the proximal housing is a receiver 370 into which a plunger 380 can be slidably placed and retained. The top of the receiver includes a slot 372 for receiving a cartridge 392 that carries an anchor to be implanted. The cartridge 392 can be seen to have at least first and second ends of a working suture 393 extending therefrom.

The delivery device is shown relative to a patient 400 having a patient portal 402, which may be for example a shoulder portal that is formed for performing arthroscopic surgery. In the example shown, the removed cartridge 392 is shown with the working suture 393 extending on either side thereof. The physician may pull the cartridge away from the magazine and the delivery device, as well as the portal 402, in order to floss the working suture 393 so that an amount of slack is available on either side of the anchor contained in the cartridge 392. The purpose of this maneuver is to ensure that as the anchor is advanced through the delivery device and into the patient, there will be enough slack to make this passage easy. That is, while it is possible to floss the suture through the anchor during delivery and implantation, it may be preferable to generate slack before the implantation to make advancement of the anchor into position relatively easier. Once the anchor is positioned, the extra slack can be taken out as the physician tensions the working suture to create a stitch between the anchor being toggled and a previously placed anchor.

Opposite the plunger 380 is a magazine 390 that can be releasably secured to the proximal housing 310 and carries a plurality of cartridges 391. A cartridge ejector is shown at 394 for ejecting cartridges 391/392 one at a time. The magazine is shown with 7 cartridges 391 therein, the $8^{th}$ cartridge 392 having already been ejected. In the example shown, at least one additional cartridge has already been ejected and used, since the working suture 393 can be seen to extend into the elongate tube 306 and into the patient portal 402. It will be understood as well that the magazine is carried on receiver 398. Greater detail regarding the magazine and its use can be found in U.S. patent application Ser. No. 17/551,811, filed on Dec. 15, 2021 and titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosure of which is incorporated herein by reference.

As illustrated in FIG. 11A, the plunger itself is shown at 380, in an extended position relative to a receiver 370. When a cartridge is placed in the slot 372, the plunger 380 can be depressed at an appropriate time during an anchor implantation procedure. Doing so laterally transfers the anchor from the cartridge into the bore through the length of the delivery device. The anchor is then ready to be inserted by advancing the bone punch 320 (or anchor insertion tool for a soft anchor) through the proximal housing and down the anchor delivery lumen. The plunger prepares the anchor for delivery by pushing the anchor laterally to the midline of the anchor delivery tube, and holds the anchor in position until the bone punch is advanced to push the anchor down the anchor delivery tube.

In some examples, and as further explained in U.S. patent application Ser. No. 17/551,811, filed on Dec. 15, 2021 and titled DELIVERY DEVICE FOR IMPLANTING KNOTLESS MICRO-SUTURE ANCHORS AND ANCHOR ARRAYS FOR ATTACHMENT OF SOFT TISSUE TO BONE, depressing the plunger 380 modifies the position of various features internal to the housing 310 which determine what happens when the trigger is actuated. In an example, when the plunger is 380 is in the extended position, actuating the trigger will mechanically pull on the bone punch 320 to retract it from a fully extended position (FIG. 10C), but does not retract the nub and in fact leaves the nub and anchor delivery tool in an extended, locked position, transitioning the distal end of the anchor delivery tool from the configuration of FIG. 10C to the configuration of FIG. 10D. The same actuation of the trigger with the plunger 380 in a depressed position, which would occur after the plunger is depressed to move an anchor into the anchor delivery tube and after the bone punch (or anchor insertion tool for a soft anchor) has been fully inserted, will retract both the bone punch (or anchor insertion tool) and the nub, transitioning the distal end of the anchor delivery tool from the configuration of FIG. 10C to the configuration of FIG. 10B. Illustrative examples of mechanical features to provide this functionality are disclosed in the Ser. No. 17/551,811 Application, the disclosure of which is incorporated herein by reference.

FIGS. 11B-11E illustrate a cartridge for holding an anchor. Starting with FIG. 11B, a cartridge 500 is illustrated with a handle 502 adapted for grasping by the user/physician. An inner holder is shown at 510, and is surrounded by a cover 520. The inner holder 510 secures an anchor 100 between an upper anchor support 511 and a boss 512. In the configuration shown in FIG. 11B, the cartridge is "closed" in that the anchor 100 cannot be removed.

Figure 11C:
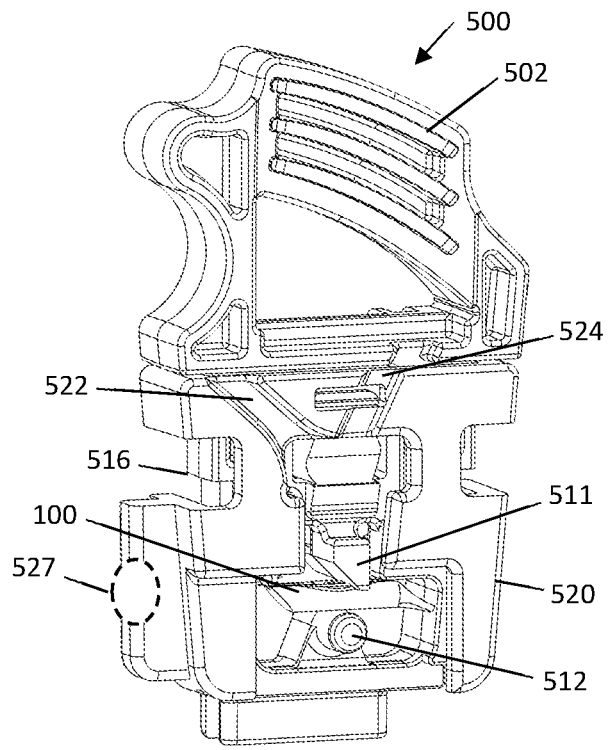

FIG. 11C shows the cover 520 raised to an "open" position in which the anchor 100 is no longer secured by the cover 520. The cover defines two channels at 522, 524. First channel 522 provides a path for the working suture out of the cartridge 500, and second channel 524 provides a path for the suture lock, as will be further detailed below. The cover 520 may be spring biased to the closed position, if desired, to prevent inadvertent removal of the anchor 100 during handling. Alternatively, the cover 520 can include detents to hold the cover in a closed position until pressure is applied during insertion. In addition, the upper anchor support 511 and boss 512 are spaced so that the anchor 100 is held in position against falling out.

An alternative design may have the inner holder 510 open in alignment with slot 527 to allow anchor removal in an axial, rather than lateral direction. For such an alternative, in an example, the upper anchor support 511 and boss 512 would be positioned higher up on the inner holder, such that the anchor 100 would be held at position 516 as shown in FIG. 11C. Doing so may remove the need to have a plunger on the proximal housing of the anchor delivery tool.

Figure 11D:
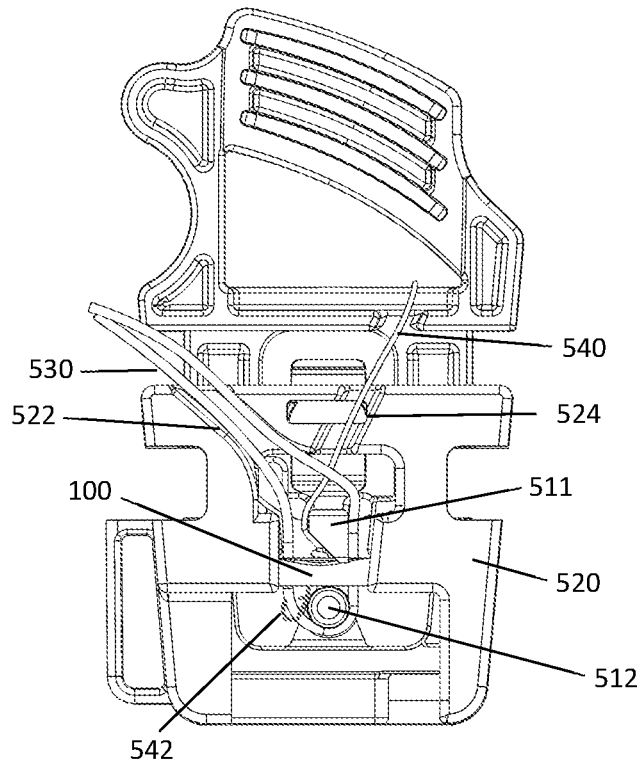

FIG. 11D shows the cartridge 500 in the closed position again with the cover down. The working suture 530 is now shown passing through first channel 522. The suture lock is shown as well, with the free end 540 of the suture lock passing through second channel 524 and the locking loop shown at 542. As can be seen, the boss 512 holds the working suture 530 away from the underside of the anchor 510, making flossing of the working suture easier prior to release of the anchor 510 from the cartridge. That is, because the bottom side of the anchor 510 may include a channel that makes flossing of the working suture therethrough more difficult, keeping the working suture 530 away from the bottom side of the anchor 100 may make flossing easier. Also, when the working suture 530 is pulled close to the bottom side of the anchor 100, the path that must be navigated when flossing includes first and second near ninety degree turns, increasing friction as the working suture 530 is flossed. Therefore, the boss 512 can be seen to make flossing easier in some examples. In other examples, the boss 512 may be designed so that the working suture does not wrap around it, and instead a simple support on the bottom side of the anchor 100 may be provided, with the working suture then resting between the support and the bottom side of the anchor. It may also be noted that having the working suture placed as shown may aid in retaining the anchor in place until it is ejected by the insertion of the plunger in the examples shown above.

Figure 11E:
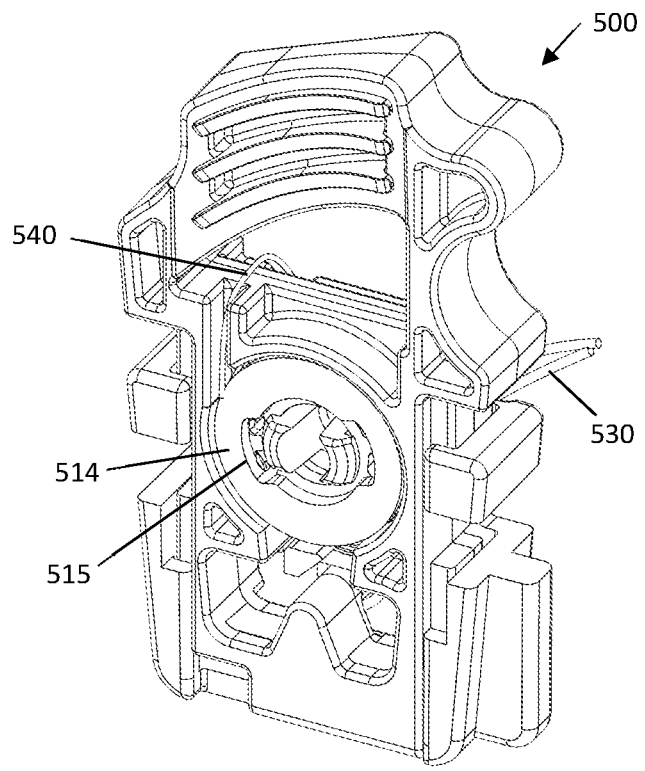

FIG. 11E shows the back side of the cartridge 500. Of note here, the free end 540 of the locking loop 542 passes into a channel and then to a spool 514. In an example, the free end 540 is attached to the spool 514, such as by a knot, so that the free end can be pulled a select distance (10 to 20 cm, for example) before reaching a point where it can no longer unspool. When the physician seeks to use the locking loop, the cartridge 500 can be grasped and pulled until the spool runs out. The physician can then pull on the cartridge and therefore on the free end of the locking loop until the locking loop secures the working suture position and, then, breaks at the break knot (or other preferential point of failure), as described below and above. The result is that the physician can manually grasp the cartridge to easily lock the locking loop and break the free end of the locking loop without needing a special tool and/or without needing to attempt to grasp the thin cord of the free end of the locking loop. It can be observed that the spool 514 includes inner features 515 allowing a tool to be inserted and twisted to spool the free end 540 of the locking loop onto the spool 514. As with the steps of toggling and/or tensioning a stitch, the distal end of the anchor delivery tool may be used to apply exterior pressure on the tendon as the locking loop is tightened and the free end is broken off.

Additional details regarding an illustrative magazine and its use may be found in U.S. patent application Ser. No. 17/551,811, filed on Dec. 15, 2021 and titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosure of which is incorporated herein by reference.

It should be noted that the illustrative anchor implantation system shown is but one example of how the presently disclosed anchor system may be implanted. For example, a system that fully withdraws the distal end of the bone punch back to the proximal housing as shown may not be necessary. Separate cartridges for each bone anchor are illustrated in the implantation system; in other examples, several anchors may be disposed together in one cartridge in a longitudinal fashion, for example, for sequential loading. Another anchor delivery tool is disclosed, for example, in U.S. Provisional Patent Application Ser. No. 63/172,629, filed Apr. 8, 2021 and titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosure of which is incorporated herein by reference. Rather than lateral release of an anchor from a cartridge, an axial release may be used. In some examples, a cartridge can be omitted entirely. Any suitable implantation system may be used, as desired.

Figure 12A:
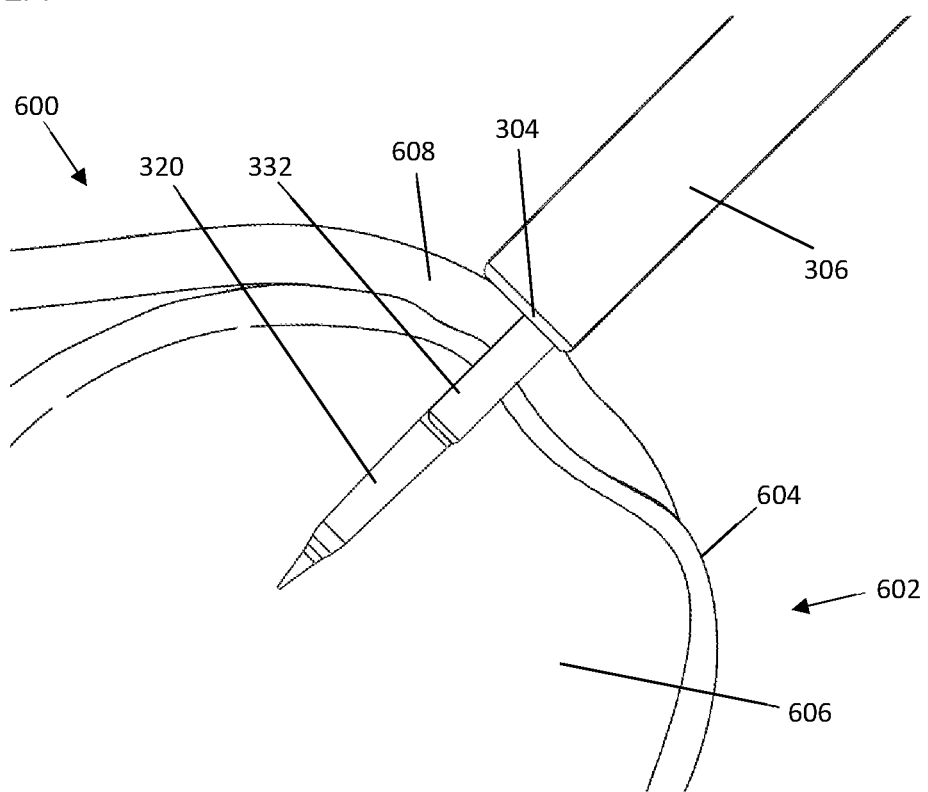
FIGS. 12A-12G illustrate the steps for implanting exemplary anchors of the current invention.

In FIGS. 12A through 12G, an exemplary method for implanting individual and an array of anchors is depicted. Referring first to FIG. 12A, a schematic of select parts of the shoulder rotator cuff 600 is depicted in order to explain the methods of implantation. The illustration includes a portion of the humeral head 602 shown including an outer cortical shell layer 604 and an inner cancellous bone material 606. A tendon, in this case the supraspinatus tendon 608 is shown overlaying a portion of the humeral head where is attached to the footprint. The method is a transtendinous or through the tendon repair. The tendon 608 is first positioned in a desired location for reattachment to bone in the footprint of original attachment.

The delivery device disclosed herein, or similar is then utilized to implant the type suture anchor through the tendon 608. To begin the delivery device is set with the distal nub 332 extending from the distal end of the implant delivery tube 330 and elongate tube 306. The bone punch 320 is fully inserted distally so that it extends beyond the distal end of the nub 332 and is locked in place, as is the nub locked in place. The device as configured is positioned on the tendon at the desired anchor placement and pounded in until the distal end of the outer tubular member is in contact with the tendon as shown in FIG. 12A. At this point the nub 332 extends through at least a portion of the cortical shell 604 (in thinner bone the nub 332 can extend into the cancellous bone 606) and the distal end of the bone punch 320 extends deeper into the cancellous bone 606. To achieve the desired depth of implantation to assure toggling, the bone punch extends beyond the elongate tube 306 distal end a distance of greater than or equal to about 20 mm, Further, to assure nub registration with the bone hole, the nub portion 332 extends beyond the elongate tube 306 distal end a distance of about 6 to about 10 mm.

Figure 12B:
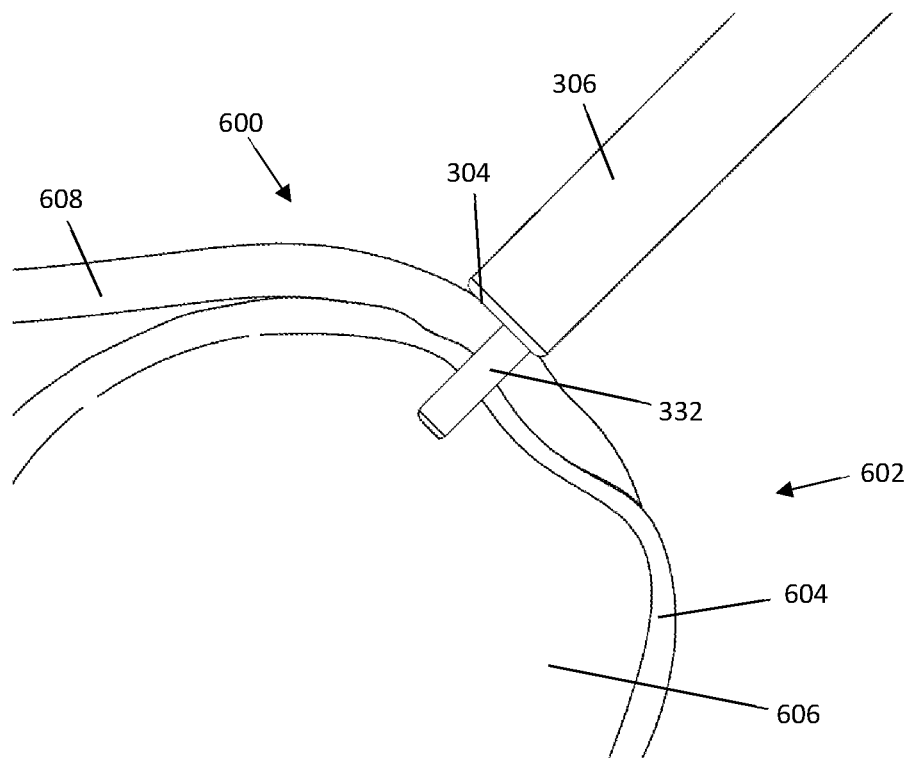

As depicted in FIG. 12B, the bone punch 320 is then retracted while maintaining the elongate tube 306 and nub portion 332 in place, with the nub portion 332 providing registration with the formed hole in the bone. Absent such registration with the bone hole by the nub portion 332, the location under the tendon would be lost and it would be very difficult to feed an anchor through the tendon which would tend to fill the hole through which the bone punch traveled. In some examples, as described above, this step of the method may be performed by depressing a trigger on an implant tool where the implant tool is configured to maintain the nub portion 332 extended under certain circumstances (for example, with the slide stop in place) while applying a positive retraction force to the bone punch 320.

Figure 12C:
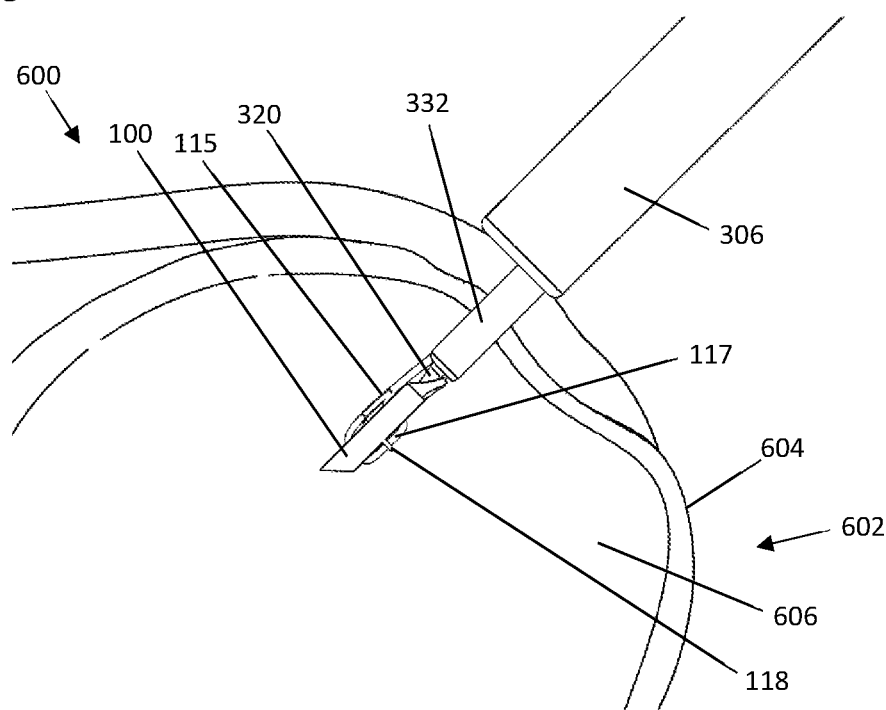

The first type anchor is transferred or inserted into the proximal portion of the anchor delivery tube inside the elongate tube 306. As shown in FIG. 12C, the bone punch 320 is then reinserted into the lumen of the anchor delivery tube and advanced distally. The example shown illustrates a toggle-type anchor with a toggle body 100 being inserted; the skilled person will understand variation in steps that would occur for the other anchor types disclosed above.

Figure 12D:
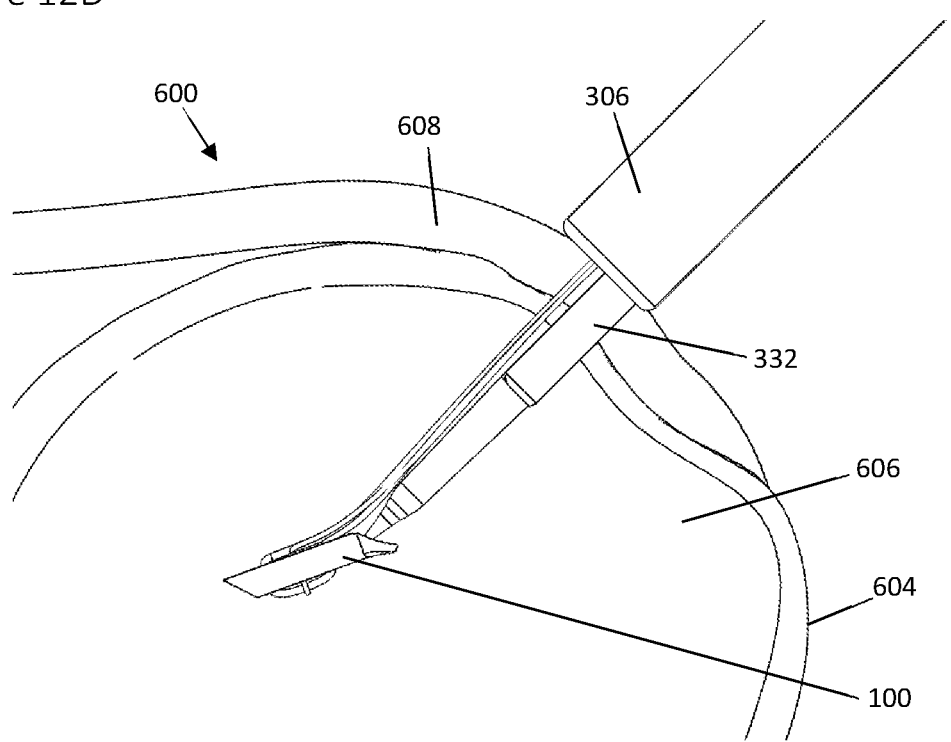

As shown in FIG. 12C, the toggle body 100 of the anchor is pushed out the distal end by the bone punch 320. The bone punch 320 continues to be advanced in the distal direction to its original depth to push the toggle body 100 into the bone, as shown in FIG. 12D. It has been found that pushing the proximal end of the anchor deep into the bone with the toggle body 100 having an angled distal end causes or at least initiates rotation of the toggle body 100. This initial rotation assures continued rotation upon pulling tension on the working suture 115 outside the body.

Figure 12E:
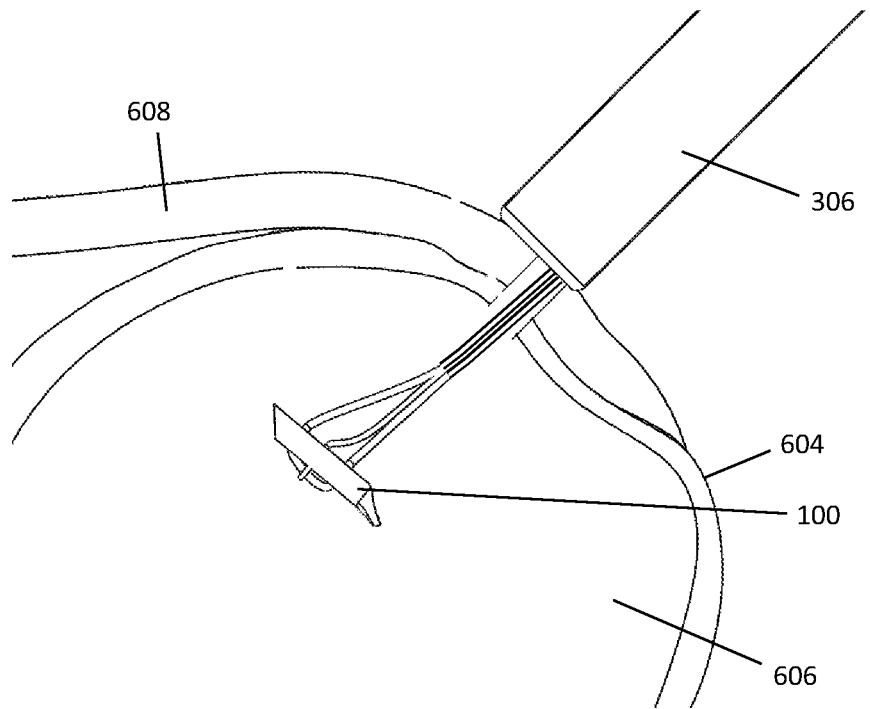

As shown in FIG. 12E, the bone punch 320 and nub 332 are then retracted by the application of positive force by the trigger (as discussed above), as well as with spring action. This assures the nub 332 does not cut or fray the working suture. The bone hole remains shown in the drawings. The distal portion of the working suture extending from the distal passage is then pulled to complete the toggling of the anchor as aided by the proximal fins on the toggle body.

Figure 12F:
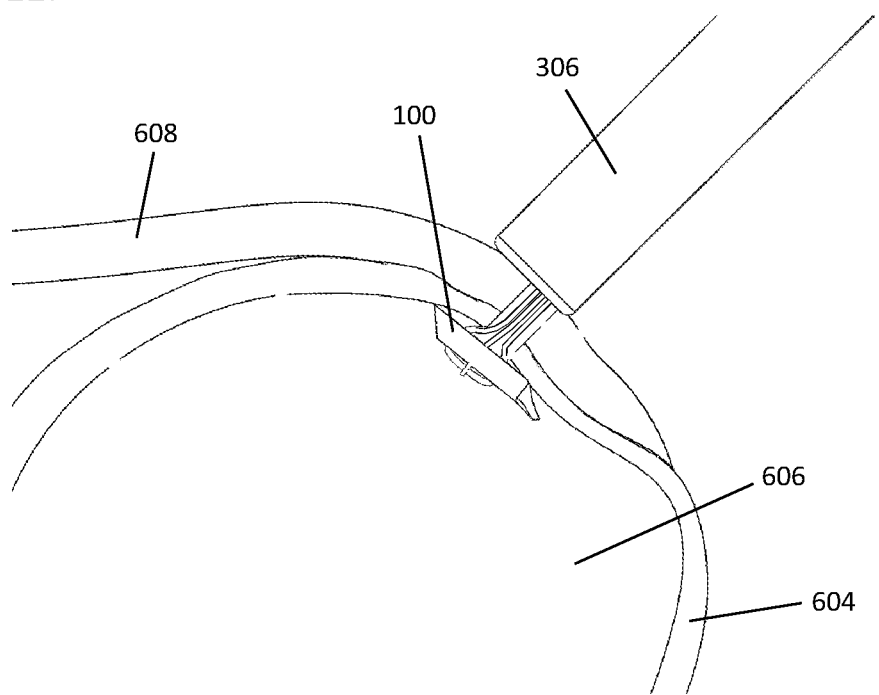
Figure 12G:
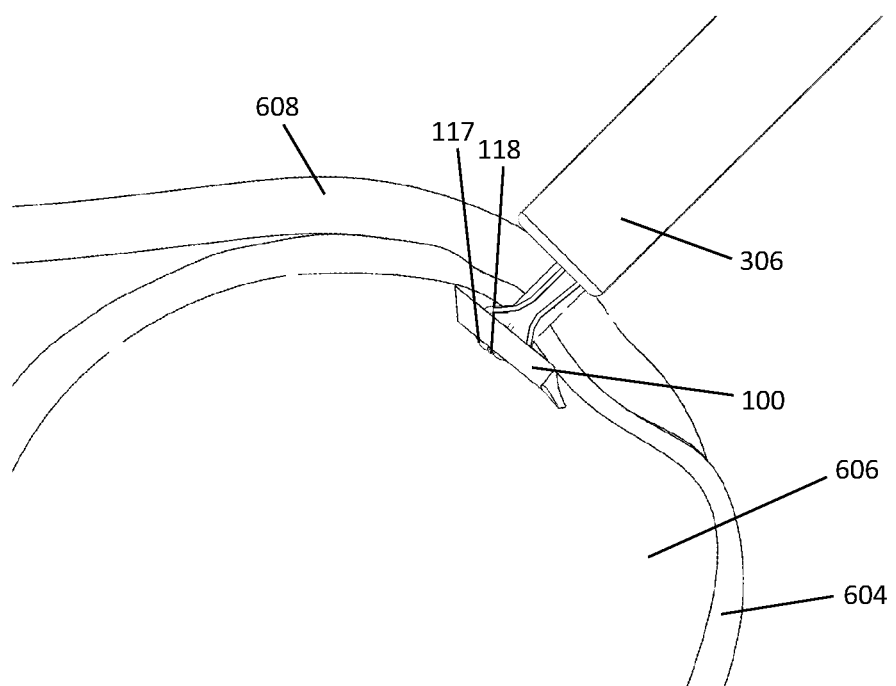

With continued tension on the working suture, the toggle body 100 is pulled toward the inside surface of the cortical shell of the bone as shown in FIG. 12F. To aid this step, the anchor delivery tool distal end may be pressed against the tendon to provide a counterforce against pullout during toggling and/or suture tensioning; that is, as the anchor is toggled and the suture is tensioned, the toggle body 100 may reach and press against the cortical shell. Additional counterforce can be applied in particular in regions of thinner cortical shell, such at the edges or outside of a tear footprint, and/or between the greater and lesser tubercles of the humerus. As depicted in FIG. 12G, once the working suture is tensioned, the locking suture is tensioned to close the locking loop 118 around the working suture and fix the working suture relative to the toggle body 100. In some examples, the locking suture is broken during this step at the knot which is at or inside the central bore of the anchor 100, thus, FIG. 12G shows only the working suture extending back into the elongate tube 306.

With implantation of the first anchor, the working suture is simply locked as it cannot be tensioned to form a stitch until the second anchor is implant. In some examples, the first anchor in a chain of anchors can be pre-locked for this purpose; in other examples the surgeon will lock the first anchor suture lock at the time of implant. Therefore, in preferred methods, the second anchor is implanted repeating the above steps, except to the extent that the suture lock is differently engaged. As the working suture is pulled to toggle the anchor, any loose working suture between the first and second anchors is pulled through to form the tensioned stitch. During suture tensioning the distal end of the elongate tube 306 can be maintained against the outer surface of the tendon to prevent pullout or even possible bone fracture at the cortical shell. Once properly tensioned, the second anchor is locked. These steps are repeated for the rest of the anchors in an array. In some examples, one or more intermediate anchors do not include a suture lock, as noted above, though other steps of the method shown in FIGS. 12A-12G may remain the same.

The preceding provides a relatively complete description of the anchor itself, pre-strung anchor arrays, suture lock, cartridge, magazine, and anchor delivery tool. A range of inventions are thus disclosed, and not all components or parts needs to be used together. For example, the delivery tool may be configured to for use with other anchors, cartridges, magazines, etc. Likewise, the anchors may be used in different configurations with other working suture and suture lock arrangements, other cartridges, magazines and delivery tools. Thus the overall combination shown can be modified in a variety of ways.

Additional features and alternative designs for various components, subassemblies and assemblies may be found in the following patent applications, each of which is incorporated herein by reference:

U.S. Prov. Pat. App. No. 63/172,564, filed Apr. 8, 2021, titled KNOTLESS MICRO SUTURE ANCHORS AND ANCHOR ARRAYS FOR ANATOMICAL ATTACHMENT OF SOFT TISSUE TO BONE, and U.S. patent application Ser. No. 17/551,588, filed on Dec. 15, 2021 and titled KNOTLESS MICRO SUTURE ANCHORS AND ANCHOR ARRAYS FOR ANATOMICAL ATTACHMENT OF SOFT TISSUE TO BONE.

U.S. Prov. Pat. App. No. 63/172,565, filed Apr. 8, 2021, titled TENSIONABLE AND LOCKABLE MICRO SUTURE ANCHORS AND ANCHOR ARRAYS FOR ANATOMICAL ATTACHMENT OF SOFT TISSUE TO BONE, and U.S. patent application Ser. No. 17/551,709, filed on Dec. 15, 2021 and titled TENSIONABLE AND LOCKABLE MICRO SUTURE ANCHORS AND ANCHOR ARRAYS FOR ANATOMICAL ATTACHMENT OF SOFT TISSUE TO BONE.

U.S. Prov. Pat. App. No. 63/172,613, filed Apr. 8, 2021, titled KNOTLESS MICRO SUTURE ANCHOR ARRAY FOR HIGH DENSITY ANATOMICAL ATTACHMENT OF SOFT TISSUE TO BONE and U.S. patent application Ser. No. 17/551,728, filed on Dec. 15, 2021 and titled KNOTLESS MICRO SUTURE ANCHOR ARRAY FOR HIGH DENSITY ANATOMICAL ATTACHMENT OF SOFT TISSUE TO BONE.

U.S. Prov. Pat. App. No. 63/172,629, filed Apr. 8, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, and U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, and U.S. patent application Ser. No. 17/551,811, filed on Dec. 15, 2021 and titled DELIVERY DEVICE FOR IMPLANTING KNOTLESS MICRO-SUTURE ANCHORS AND ANCHOR ARRAYS FOR ATTACHMENT OF SOFT TISSUE TO BONE.

U.S. Prov. Pat. App. No. 63/172,624, filed Apr. 8, 2021, titled CARTRIDGE DEVICE FOR SUTURE ANCHOR AND SUTURE MANAGEMENT DURING IMPLANTATION OF A MICRO SUTURE ANCHOR ARRAY, and U.S. patent application Ser. No. 17/551,838, filed on Dec. 15, 2021 and titled CARTRIDGE DEVICE FOR SUTURE ANCHOR AND SUTURE MANAGEMENT DURING IMPLANTATION OF A MICRO SUTURE ANCHOR ARRAY.

U.S. Prov. Pat. App. No. 63/172,568, filed Apr. 8, 2021, titled LOCKING SUTURE CONSTRUCT FOR TENSIONED SUTURE TO SUTURE BRIDGES IN ANCHOR ARRAYS FOR ATTACHING SOFT TISSUE TO BONE and U.S. patent application Ser. No. 17/551,860, filed on Dec. 15, 2021 and titled LOCKING SUTURE CONSTRUCT FOR TENSIONED SUTURE TO SUTURE STITCHES IN ANCHOR ARRAYS FOR ATTACHING SOFT TISSUE TO BONE.

U.S. Prov. Pat. App. No. 63/172,630, filed Apr. 8, 2021, titled METHODS FOR TRANSTENDINOUS IMPLANTATION OF KNOTLESS MICRO SUTURE ANCHORS AND ANCHOR ARRAYS, and U.S. patent application Ser. No. 17/551,885, filed on Dec. 15, 2021 and titled METHODS FOR TRANSTENDINOUS IMPLANTATION OF KNOTLESS MICRO SUTURE ANCHORS AND ANCHOR ARRAYS.

Each of these non-limiting examples can stand on its own or can be combined in various permutations or combinations with one or more of the other examples.

The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. A method for repairing a torn rotator cuff tendon by reattachment to a humeral head utilizing a seam-like row of serial stitches extending over incremental portions of the torn rotator cuff tendon, the method comprising the steps of:
   providing a pre-strung plurality of anchors including a first anchor, a plurality of intermediate anchors and a final anchor with each of the pre-strung plurality of anchors having a bone hole insertion diameter of less than or equal to about 3 mm, wherein the first anchor includes a length of working suture affixed thereto, each of the plurality of intermediate anchor having at least one passage therethrough with the length of working suture slidably and serially threaded through the at least one passage of each of the plurality of intermediate anchor and the final anchor also having at least one passage therethrough with the length of working suture slidably threaded therethrough and further including a means for locking the length of working suture relative to the final anchor;
   implanting each of the pre-strung plurality of anchors in a single row through the torn rotator cuff tendon, the pre-strung plurality of anchors each implanted in a bone hole, with the plurality of intermediate anchors placed in bone holes formed in an original footprint of the torn rotator cuff tendon with spacing between adjacent anchors a distance of about 10 mm or less as measured from center of bone hole to center of bone hole;
   applying tension to the length of working suture after implantation of each plurality of intermediate anchor and the final anchor implantation to form a series of single suture tensioned stitches between the pre-strung plurality of anchors; and
   securing the length of working suture as tensioned to the final anchor with the means for locking the length of working suture.

2. The method of claim 1, wherein the plurality of intermediate anchors includes six anchors.

3. The method of claim 1, wherein the means for locking the length of working suture is a locking loop, the locking loop extending adjacent the final anchor wherein the locking loop encircles a portion of the length of the working suture, the locking loop having a first open position allowing the length of working suture to slide through the locking loop and a second closed position engaging the length of working suture and preventing sliding of the length of working suture within the locking loop.

4. The method of claim 1, wherein the means for locking the length of working suture is a knot tied in the length of working suture adjacent the passage in the final anchor after tensioning.

5. The method of claim 1, wherein the means for locking the length of working suture is a one-way slip knot that allows sliding of the length of working suture in a first direction but prevents sliding in an opposite direction, wherein the step of applying tension to the length of working suture is performed by pulling the length of working suture in the first direction.

6. The method of claim 1, wherein the means for locking the length of working suture is a set of angled projections in the passages of the pre-strung plurality of anchors that allow the length of working suture movement in a first direction but prevent the length of working suture movement in a direction opposite the first direction, and the step of applying tension to length of working suture is performed by pulling the length of working suture in the first direction.

7. The method of claim 1, wherein the means for locking the length of working suture is mechanical lock that compresses and secures the length of working suture to the final anchor when activated.

8. The method of claim 1, wherein each plurality of intermediate anchor further includes means for locking the length of working suture thereto.

9. A method for securing a supraspinatus tendon and an infraspinatus tendon to a humeral head, the method comprising the steps of:
provides a first anchor having a length of a working suture secured thereto, the first anchor having an insertion diameter in a bone hole of less than or equal to about 3 mm;
implanting the first anchor through either of the supraspinatus tendon and the infraspinatus tendon into the humeral head within a medial half of an original combined footprint of attachment of the supraspinatus and infraspinatus tendons to the humeral head;
providing a plurality of intermediate anchors, each plurality of intermediate anchor slidably received on the length of working suture, each plurality of intermediate anchor having a passage therethrough wherein each plurality of intermediate anchor is configured for insertion in a bone hole having a diameter of less than or equal to about 3 mm;
implanting the plurality of intermediate anchors through the supraspinatus and infraspinatus tendons into bone holes formed in the humeral head in a serial row within the medial half of the original combined footprint, wherein the first of the plurality of intermediate anchors is spaced from the first anchor by a distance of less than or equal to about 10 mm measured from center of bone hole to center of bone hole and each subsequently implanted plurality of intermediate anchors is spaced from the just previously implanted adjacent plurality of intermediate anchors by a distance of less than about 10 mm measured from center of bone hole to center of bone hole;
providing a final anchor, the final anchor slidably received on the length of working suture, the final anchor having a passage therethrough wherein the final anchor is configured for insertion in a bone hole having a diameter of less than or equal to about 3 mm wherein the final anchor further includes means for selectively locking the length of working suture relative to the final anchor;
implanting the final anchor through either of the supraspinatus tendon and the infraspinatus tendon into a bone hole formed in the humeral head within the medial half of the original combined footprint, wherein the final anchor is spaced from the last plurality of intermediate anchors by a distance of less than or equal to about 10 mm measured from center of bone hole to center of bone hole;
tensioning the length of working suture at locations along its length to form a stitch extending between each anchor in series to hold the supraspinatus tendon and the infraspinatus tendon against the humeral head; and,
securing the tensioned length of working suture to the final anchor utilizing the means for selective locking to maintain desired tension in the formed individual stitches.

10. The method of claim 9, wherein the plurality of intermediate anchors includes six anchors.

11. The method of claim 9, wherein the means for locking the length of working suture is a locking loop, the locking loop extending adjacent the final anchor wherein the locking loop encircles a portion of the length of the working suture, the locking loop having a first open position allowing the length of working suture to slide through the locking loop and a second closed position engaging the length of working suture and preventing sliding of the length of working suture within the locking loop.

12. The method of claim 9, wherein the means for locking the length of working suture is a knot tied in the length of working suture adjacent the passage in the final anchor after tensioning.

13. The method of claim 9, wherein the means for locking the length of working suture is a one-way slip knot that allows sliding of the length of working suture in a first direction but prevents sliding in a direction opposite the first direction, wherein the step of tensioning the length of working suture includes pulling the length of working suture in the first direction.

14. The method of claim 9, wherein the means for locking the length of working suture is a one way passage through the final anchor that includes angled projections that allow the length of working suture movement in a first direction but prevents moving the length of working suture movement in a direction opposite the first direction wherein the step of tensioning the length of working suture includes pulling the length of working suture in the first direction.

15. The method of claim 9, wherein the means for locking the length of working suture is a mechanical lock that compresses and secures the length of working suture to the final anchor when activated.

16. The method of claim 9, wherein each intermediate anchor further includes means for locking the length of working suture thereto.

17. A method for repairing a torn rotator cuff tendon by reattachment to the humeral head utilizing a seam-like row of serial stitches extending over incremental portions of the torn rotator cuff tendon in an original footprint of the torn rotator cuff tendon on the humeral head, the method comprising the steps of:
providing a pre-strung plurality of anchors, including a first anchor, a plurality of intermediate anchors and a final anchor with each of the pre-strung plurality of anchors having a bone hole insertion diameter of less than or equal to about 3 mm, wherein the first anchor includes a length of working suture affixed thereto, each of the plurality of intermediate anchors having at least one passage therethrough with the length of working suture slidably and serially threaded through the at least one passage of each of the plurality of intermediate anchor and the final anchor also at least one passage therethrough with the length of working suture slidably threaded therethrough and further including a separate locking loop, wherein the separate locking loop encircles a portion of the length of the working suture adjacent the final anchor and having a first position allowing the length of working suture to slide through the locking loop and a second position engaging the length of working suture and preventing sliding within the locking loop;

implanting the first anchor through the torn rotator cuff tendon into a bone hole formed in the humeral head within the original footprint;

implanting a first of the plurality of intermediate anchors of the pre-strung plurality of anchors in a bone hole formed in the original footprint a distance of about 10 mm or less from the first anchor as measured from center of bone hole to center of bone hole, then applying tension to the length of working suture extending from the first anchor and passing through the first intermediate anchor to form a single suture tensioned stitch between the first anchor and first intermediate anchor;

implanting a second of the intermediate anchors in the pre-strung plurality of anchors in the original footprint a distance of about 10 mm or less from the first intermediate anchor as measured from center of bone hole to center of bone hole, then applying tension to the length of working suture extending from the first intermediate anchor and passing through the second intermediate anchor to form a single suture tensioned stitch between the first and second intermediate anchors;

repeating the spacing distances, implanting and tensioning steps for each subsequent serial plurality of intermediate anchors and the final anchor; and, activating the locking loop to maintain tension in the created array.

18. The method of claim 17, wherein the plurality of intermediate anchors includes six anchors.

19. The method of claim 17, wherein each plurality of intermediate anchor further includes means for locking the length of working suture thereto.

20. The method of claim 17, wherein at least one of the plurality of intermediate anchor omits any means for locking the length of working suture thereto.

\* \* \* \* \*